(12) United States Patent
Blain

(10) Patent No.: US 11,801,042 B2
(45) Date of Patent: *Oct. 31, 2023

(54) METHOD OF USING A SURGICAL TISSUE RETRACTOR

(71) Applicant: Spinal Elements, Inc., Carlsbad, CA (US)

(72) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 17/126,791

(22) Filed: Dec. 18, 2020

(65) Prior Publication Data

US 2021/0169463 A1 Jun. 10, 2021

Related U.S. Application Data

(63) Continuation of application No. 16/214,442, filed on Dec. 10, 2018, now Pat. No. 10,898,174, which is a
(Continued)

(51) Int. Cl.
*A61B 17/02* (2006.01)
*A61B 5/389* (2021.01)
*A61B 17/28* (2006.01)

(52) U.S. Cl.
CPC .......... *A61B 17/0206* (2013.01); *A61B 5/389* (2021.01); *A61B 17/0218* (2013.01);
(Continued)

(58) Field of Classification Search
CPC . A61B 17/02; A61B 17/0206; A61B 17/0218; A61B 17/28; A61B 5/04; A61B 5/0488
See application file for complete search history.

(56) References Cited

U.S. PATENT DOCUMENTS

| 350,721 A | 10/1886 | Cooper |
| 569,839 A | 10/1896 | Roeloffs |

(Continued)

FOREIGN PATENT DOCUMENTS

| EP | 2 705 799 | 3/2014 |
| JP | 2010-508978 | 3/2010 |

(Continued)

OTHER PUBLICATIONS

Official Communication in Australian Application No. 2015315166, dated Apr. 24, 2019.
(Continued)

*Primary Examiner* — Christopher J Beccia
(74) *Attorney, Agent, or Firm* — Knobbe, Martens, Olson & Bear, LLP

(57) ABSTRACT

A method of performing an operation, e.g. a spinal operation, on a patient using a retractor comprising a pair of blade assemblies which are adapted to open about a set of axes that are not parallel to a third spatial axis, and further comprising a pair of arms, which are adapted to move the pair of blade assemblies apart from one another in the third spatial axis. In the method, the blade assemblies are closed to assume a low profile, inserted into a relatively small incision, and stretched apart from each other, thereby stretching the skin about the incision to form an aperture longer than the incision. The blade assemblies are then opened by rotating the blades about the set of axes, stretching the skin around the incision in a second direction that is substantially perpendicular to the first direction (i.e. the direction of the incision.)

17 Claims, 29 Drawing Sheets

Related U.S. Application Data continuation of application No. 15/602,542, filed on May 23, 2017, now Pat. No. 10,172,603, which is a continuation of application No. 15/204,329, filed on Jul. 7, 2016, now Pat. No. 9,693,763, which is a continuation of application No. 13/794,470, filed on Mar. 11, 2013, now Pat. No. 9,408,596.

(52) U.S. Cl.
CPC ............... *A61B 2017/0256* (2013.01); *A61B 2017/2837* (2013.01)

(56) References Cited

U.S. PATENT DOCUMENTS

| | | | |
|---|---|---|---|
| 1,311,313 A | 7/1919 | Brix | |
| 1,328,624 A | 1/1920 | Graham | |
| 1,613,141 A | 1/1927 | Stein | |
| 1,822,280 A | 9/1931 | Ervay | |
| 2,002,021 A * | 5/1935 | Rouse | A61B 17/6408 606/86 R |
| 2,670,731 A | 3/1954 | Zoll et al. | |
| 2,693,795 A | 11/1954 | Grieshaber | |
| 2,850,008 A | 9/1958 | Resch | |
| 3,168,093 A | 2/1965 | Gauthier | |
| 3,384,078 A | 5/1968 | Gauthier | |
| 3,522,799 A | 8/1970 | Gauthier | |
| 3,747,592 A | 7/1973 | Santos | |
| 3,782,370 A | 1/1974 | McDonald | |
| 3,965,890 A | 6/1976 | Gauthier | |
| 4,156,424 A | 5/1979 | Burgin | |
| 4,616,635 A | 10/1986 | Caspar et al. | |
| 4,667,657 A | 5/1987 | Kulik et al. | |
| 5,035,232 A | 7/1991 | Lutze et al. | |
| 5,113,846 A | 5/1992 | Hiltebrandt et al. | |
| 5,363,841 A | 11/1994 | Coker | |
| 5,618,260 A | 4/1997 | Caspar et al. | |
| 5,681,265 A | 10/1997 | Maeda et al. | |
| 5,772,583 A | 6/1998 | Wright et al. | |
| 5,928,139 A | 7/1999 | Koros et al. | |
| 5,931,777 A | 8/1999 | Sava | |
| 5,931,778 A | 8/1999 | Furnish | |
| 5,980,455 A | 11/1999 | Daniel et al. | |
| 6,042,540 A | 3/2000 | Johnston et al. | |
| 6,074,343 A | 6/2000 | Nathanson et al. | |
| 6,080,155 A | 6/2000 | Michelson | |
| 6,139,493 A | 10/2000 | Koros et al. | |
| 6,206,826 B1 | 3/2001 | Mathews et al. | |
| 6,264,650 B1 | 7/2001 | Hovda et al. | |
| 7,087,055 B2 | 8/2006 | Lim et al. | |
| 7,229,408 B2 | 6/2007 | Douglas et al. | |
| 7,390,298 B2 | 6/2008 | Chu | |
| 7,481,766 B2 | 1/2009 | Lee et al. | |
| 7,491,168 B2 | 2/2009 | Raymond et al. | |
| 7,537,565 B2 | 5/2009 | Bass | |
| 7,582,058 B1 * | 9/2009 | Miles | A61B 17/0293 607/2 |
| 7,594,888 B2 | 9/2009 | Raymond et al. | |
| 7,722,613 B2 | 5/2010 | Sutterlin et al. | |
| 7,785,253 B1 | 8/2010 | Arambula et al. | |
| 7,819,801 B2 | 10/2010 | Miles et al. | |
| 7,846,183 B2 | 12/2010 | Blain | |
| 7,892,173 B2 | 2/2011 | Miles et al. | |
| 7,922,658 B2 | 4/2011 | Cohen et al. | |
| 8,062,217 B2 | 11/2011 | Boucher et al. | |
| 8,062,218 B2 | 11/2011 | Sebastian et al. | |
| 8,137,284 B2 | 3/2012 | Miles et al. | |
| 8,142,355 B2 | 3/2012 | Blain et al. | |
| 8,192,356 B2 | 6/2012 | Miles et al. | |
| 8,303,498 B2 | 11/2012 | Miles et al. | |
| 8,303,515 B2 | 11/2012 | Miles et al. | |
| 8,353,826 B2 | 1/2013 | Weiman | |
| 8,388,527 B2 | 3/2013 | Miles et al. | |
| 8,409,091 B2 | 4/2013 | Blain et al. | |
| 8,500,634 B2 | 8/2013 | Miles et al. | |
| 8,523,768 B2 | 9/2013 | Miles et al. | |
| 8,556,808 B2 | 10/2013 | Miles et al. | |
| 8,628,469 B2 | 1/2014 | Miles et al. | |
| 8,740,786 B2 | 6/2014 | Blain et al. | |
| 8,753,270 B2 | 6/2014 | Miles et al. | |
| 8,753,271 B1 | 6/2014 | Miles et al. | |
| 8,821,396 B1 | 9/2014 | Miles et al. | |
| 8,876,904 B2 | 11/2014 | Pimenta et al. | |
| 8,915,846 B2 | 12/2014 | Miles et al. | |
| 8,945,004 B2 | 2/2015 | Miles et al. | |
| 8,986,344 B2 | 3/2015 | Sandhu | |
| 9,044,280 B1 | 6/2015 | Arambula et al. | |
| 9,050,146 B2 | 6/2015 | Woolley et al. | |
| 9,138,217 B2 | 9/2015 | Smith et al. | |
| 9,220,491 B2 | 12/2015 | Nunley et al. | |
| 9,265,490 B2 | 2/2016 | Bowman et al. | |
| 9,351,718 B1 | 5/2016 | Arambula et al. | |
| 9,408,596 B2 | 8/2016 | Blain | |
| 9,414,831 B2 | 8/2016 | Sandhu | |
| 9,451,940 B2 | 9/2016 | Spann | |
| 9,468,405 B2 | 10/2016 | Miles et al. | |
| 9,486,133 B2 | 11/2016 | Lee et al. | |
| 9,585,649 B2 | 3/2017 | Blain et al. | |
| 9,610,071 B2 | 4/2017 | Miles et al. | |
| 9,615,818 B2 | 4/2017 | Baudouin et al. | |
| 9,622,732 B2 | 4/2017 | Martinelli et al. | |
| 9,649,101 B2 | 5/2017 | Karpowicz et al. | |
| 9,693,762 B2 | 7/2017 | Reimels | |
| 9,693,763 B2 | 7/2017 | Blain | |
| 9,737,288 B2 | 8/2017 | Karpowicz et al. | |
| 9,750,490 B2 | 9/2017 | Miles et al. | |
| 9,782,158 B2 | 10/2017 | Nunley et al. | |
| 9,788,822 B2 | 10/2017 | Miles et al. | |
| 9,795,371 B2 | 10/2017 | Miles et al. | |
| 9,820,729 B2 | 11/2017 | Miles et al. | |
| 9,826,966 B2 | 11/2017 | Mast et al. | |
| 9,826,968 B2 | 11/2017 | Miles et al. | |
| 9,833,227 B2 | 12/2017 | Miles et al. | |
| 9,848,863 B2 | 12/2017 | Cryder et al. | |
| 9,861,273 B2 | 1/2018 | Weiman | |
| 9,943,301 B2 | 4/2018 | Mast et al. | |
| 10,039,539 B2 | 8/2018 | Friedrich et al. | |
| 10,076,320 B2 | 9/2018 | Mast et al. | |
| 10,085,854 B2 | 10/2018 | Spann | |
| 10,172,603 B2 | 1/2019 | Blain | |
| 10,178,987 B2 | 1/2019 | Predick | |
| 10,299,777 B2 | 5/2019 | Mast et al. | |
| 10,426,450 B2 | 10/2019 | Vogel et al. | |
| 10,898,174 B2 * | 1/2021 | Blain | A61B 17/0206 |
| 10,945,861 B2 | 3/2021 | Abdou | |
| 10,973,505 B2 | 4/2021 | Ortiz et al. | |
| 11,179,146 B2 | 11/2021 | Vogel et al. | |
| 2002/0123668 A1 | 9/2002 | Ritland | |
| 2005/0102029 A1 | 5/2005 | Blain | |
| 2005/0107877 A1 | 5/2005 | Blain | |
| 2005/0159650 A1 | 7/2005 | Raymond et al. | |
| 2005/0159651 A1 | 7/2005 | Raymond et al. | |
| 2005/0159818 A1 | 7/2005 | Blain | |
| 2005/0192574 A1 | 9/2005 | Blain | |
| 2006/0004261 A1 | 1/2006 | Douglas | |
| 2006/0074278 A1 | 4/2006 | Petit et al. | |
| 2006/0074425 A1 | 4/2006 | Sutterlin et al. | |
| 2006/0106416 A1 | 5/2006 | Raymond et al. | |
| 2006/0224044 A1 | 10/2006 | Marchek et al. | |
| 2006/0235423 A1 | 10/2006 | Cantu | |
| 2007/0073111 A1 | 3/2007 | Bass | |
| 2007/0100212 A1 | 5/2007 | Pimenta et al. | |
| 2007/0185376 A1 | 8/2007 | Wilson et al. | |
| 2007/0238932 A1 | 10/2007 | Jones et al. | |
| 2008/0097164 A1 | 4/2008 | Miles et al. | |
| 2008/0114208 A1 | 5/2008 | Hutton et al. | |
| 2008/0132766 A1 | 6/2008 | Dant et al. | |
| 2008/0183046 A1 | 7/2008 | Boucher et al. | |
| 2008/0188718 A1 | 8/2008 | Spitler et al. | |
| 2009/0048668 A1 | 2/2009 | Wilson et al. | |
| 2010/0114110 A1 | 5/2010 | Taft et al. | |
| 2011/0034777 A1 | 2/2011 | Ames et al. | |
| 2011/0130793 A1 | 6/2011 | Woolley et al. | |
| 2011/0224497 A1 | 9/2011 | Weiman et al. | |

(56) References Cited

U.S. PATENT DOCUMENTS

| | | |
|---|---|---|
| 2012/0245431 A1 | 9/2012 | Baudouin et al. |
| 2012/0245432 A1 | 9/2012 | Karpowicz et al. |
| 2013/0158359 A1 | 6/2013 | Predick et al. |
| 2013/0190575 A1 | 7/2013 | Mast et al. |
| 2013/0261401 A1 | 10/2013 | Hawkins et al. |
| 2014/0024900 A1 | 1/2014 | Capote et al. |
| 2014/0148652 A1 | 5/2014 | Weiman |
| 2015/0230787 A1 | 8/2015 | Friedrich et al. |
| 2015/0250466 A1 | 9/2015 | Thornburg |
| 2015/0250467 A1 | 9/2015 | Higgins |
| 2016/0317137 A1 | 11/2016 | Predick et al. |
| 2019/0083081 A1 | 3/2019 | Ortiz et al. |
| 2019/0350573 A1 | 11/2019 | Vogel et al. |
| 2021/0085306 A1 | 3/2021 | Clauss et al. |
| 2021/0244398 A1 | 8/2021 | Ortiz et al. |
| 2022/0079573 A1 | 3/2022 | Ortiz et al. |
| 2022/0096072 A1 | 3/2022 | Vogel et al. |

FOREIGN PATENT DOCUMENTS

| | | |
|---|---|---|
| JP | 2013-521896 | 6/2013 |
| JP | 2013-537467 | 10/2013 |
| JP | 2014-515646 | 7/2014 |
| WO | WO 2006/042241 | 4/2006 |
| WO | WO 2012/026981 | 3/2012 |
| WO | WO 2012/040206 | 3/2012 |
| WO | WO 2013/028571 | 2/2013 |
| WO | WO 2013/033630 | 3/2013 |
| WO | WO 2015/191836 | 12/2015 |
| WO | WO 2016/040497 | 3/2016 |
| WO | WO 2017/155718 | 9/2017 |

OTHER PUBLICATIONS

Official Communication in Australian Application No. 2015315166, dated Aug. 15, 2019.
Official Communication in European Application No. 15840714.8, dated Feb. 12, 2018.
Official Communication in Japanese Application No. 2017-513531, dated Jun. 24, 2019.
Official Communication in Japanese Application No. 2017-513531, dated May 25, 2020.
International Search Report and Written Opinion in International Application No. PCT/US2015/049211, dated Dec. 4, 2015.
International Preliminary Report on Patentability and Written Opinion in International Application No. PCT/US2015/049211, dated Mar. 23, 2017.
Official Communication in European Application No. 17763744.4, dated Nov. 12, 2019.
Invitation to Pay Additional Search Fees in International Application No. PCT/US2017/019699, dated May 24, 2017.
International Search Report and Written Opinion in International Application No. PCT/US2017/019699, dated Aug. 7, 2017.
International Preliminary Report on Patentability and Written Opinion in International Application No. PCT/US2017/019699, dated Sep. 20, 2018.
Official Communication in European Application No. 20180562.9, dated Sep. 18, 2020.
Official Communication in Japanese Application No. 2017-513531, dated Feb. 22, 2021.
International Search Report and Written Opinion in International Application No. PCT/US2020/051031, dated Dec. 8, 2020.

* cited by examiner

METHOD OF USING A SURGICAL TISSUE RETRACTOR

CROSS-REFERENCE TO RELATED APPLICATIONS

The present application is a continuation of U.S. patent application Ser. No. 16/214,442, filed Dec. 10, 2018, which is a continuation of U.S. patent application Ser. No. 15/602,542, filed May 23, 2017, which is a continuation of U.S. patent application Ser. No. 15/204,329, filed Jul. 7, 2016, which is a continuation of U.S. patent application Ser. No. 13/794,470, filed Mar. 11, 2013. The contents U.S. patent application Ser. No. 13/794,470, filed Mar. 11, 2013 are hereby incorporated by reference in its entirety.

FIELD OF THE INVENTION

The present invention relates to the field of surgery and more particularly to a retractor for use in inter alia surgery of the lower back.

BACKGROUND OF THE INVENTION

Retractors are surgical devices used to spread bodily tissues in order to allow a surgeon or surgical assistant to see and access a part of the body that is to be surgically treated. In general, retractors comprise a pair of jaws or blades that grip the bodily tissue and push it apart under the force generated by an actuator, such as a pair of scissor-like arms having a distal end and a proximal end. The proximal end generally defines a pair of handles and the distal end attaches to the pair of blades so that manipulation of the handles causes the blades to move apart from one another. Once an incision is made in the body to be operated on, the blades are inserted into the incision and the actuator is manipulated to move the blades of the retractor apart, thus spreading the tissue and providing an aperture through which the surgeon can access visualize the tissue to be surgically treated. One problem with this type of retractor is that the aperture size is generally limited by the size of the incision, meaning that a large aperture requires a relatively large incision. The drawback to this arrangement is that larger incisions result in the need for longer periods for healing of the incision. There is thus a need for a surgical retractor that is capable of creating a relatively large aperture using a relatively small incision, thereby reducing the invasiveness of the surgical procedure, post-operative healing times and patient discomfort.

SUMMARY

One embodiment comprises a system for creating an operative corridor in a human body, comprising: a probe, wherein the probe is configured to be placed through the tissues of a patient from the surface of the tissue to a location of interest; a retractor system, wherein the retractor system comprises retractor blades having an internal space, wherein the internal space is substantially the same shape as the probe such that the internal space will slip over the probe when the probe is inserted into the tissues of the patient.

Another embodiment comprises a method of accessing a spine. The method includes forming an incision in tissue; placing a probe into the incision; engaging an end of the probe with an intervertebral disc space; positioning a mating retractor blade system over the probe; sliding the mating retractor blade system down and over the length of the probe; and activating the mating retractor blade system to open the mating retractor blade system to create an operative corridor.

Another embodiment comprises a method of accessing a surgery site that includes forming an incision in tissue; placing a probe into the incision; anchoring an end of the probe at the surgery site; positioning a mating retractor blade system over the probe; sliding the mating retractor blade system down the length of the probe; and activating the mating retractor blade system to open the mating retractor blade system to create an operative corridor.

Another embodiment comprises a method of accessing a human spine that includes forming an incision in tissue; inserting an endoscope into the incision, wherein the endoscope is configured to allow safe navigation to the spine; sliding a mating retractor system in a close configuration over the endoscope; sliding the mating retractor system down and over at least a portion of the endoscope into the incision in tissue; and activating the mating retractor system to create an operative corridor in the tissue.

Another embodiment comprise a retractor that includes a first blade assembly comprising a first blade rotatable about a first axis, a second blade rotatable about said first axis and an adjuster in mechanical communication with the first and second blades and adapted to rotate the first and second blades relative to each other about said first axis. A second blade assembly includes at least a third blade rotatable about a second axis and optionally a fourth blade rotatable about said second axis and, when said fourth blade is present in said second blade assembly. An adjuster is in mechanical communication with the third and fourth blades and adapted to rotate the third and fourth blades relative to each other about said second axis, wherein said second axis is different from said first axis. The retractor also includes means for moving said first blade assembly relative to said second blade assembly along a third axis that is not parallel to said first and second axes, wherein the first blade assembly moves while the second blade assembly remains substantially stationary.

Another embodiment comprises a retractor that includes a first blade assembly comprising a first blade rotatable about a first axis, a fixed second blade and an adjuster in mechanical communication with the first and second blades and adapted to rotate the first and second blades relative to each other about said first axis; a second blade assembly comprising at least a third blade rotatable about a second axis wherein said second axis is different from said first axis; and wherein said first blade assembly is movable relative to said second blade assembly along a third axis that is not parallel to said first and second axes; wherein said first blade assembly is configured to detachably separate from said second blade assembly when said retractor is in an open configuration.

In certain embodiments, the retractor (surgical retractor) can comprise (a) a first blade assembly comprising a first blade rotatable about a first axis, a second blade rotatable about said first axis and an adjuster in mechanical communication with the first and second blades and adapted to rotate the first and second blades relative to each other about said first axis; (b) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (c) a means for moving said first blade assembly relative to said second blade assembly along a third axis that is not parallel to said first and second axes.

Incorporation by Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 30 and 31 show the relationship between the angles of slots in the first blade and the second blade of the blade assembly.

DETAILED DESCRIPTION OF THE INVENTION

Figure 1:
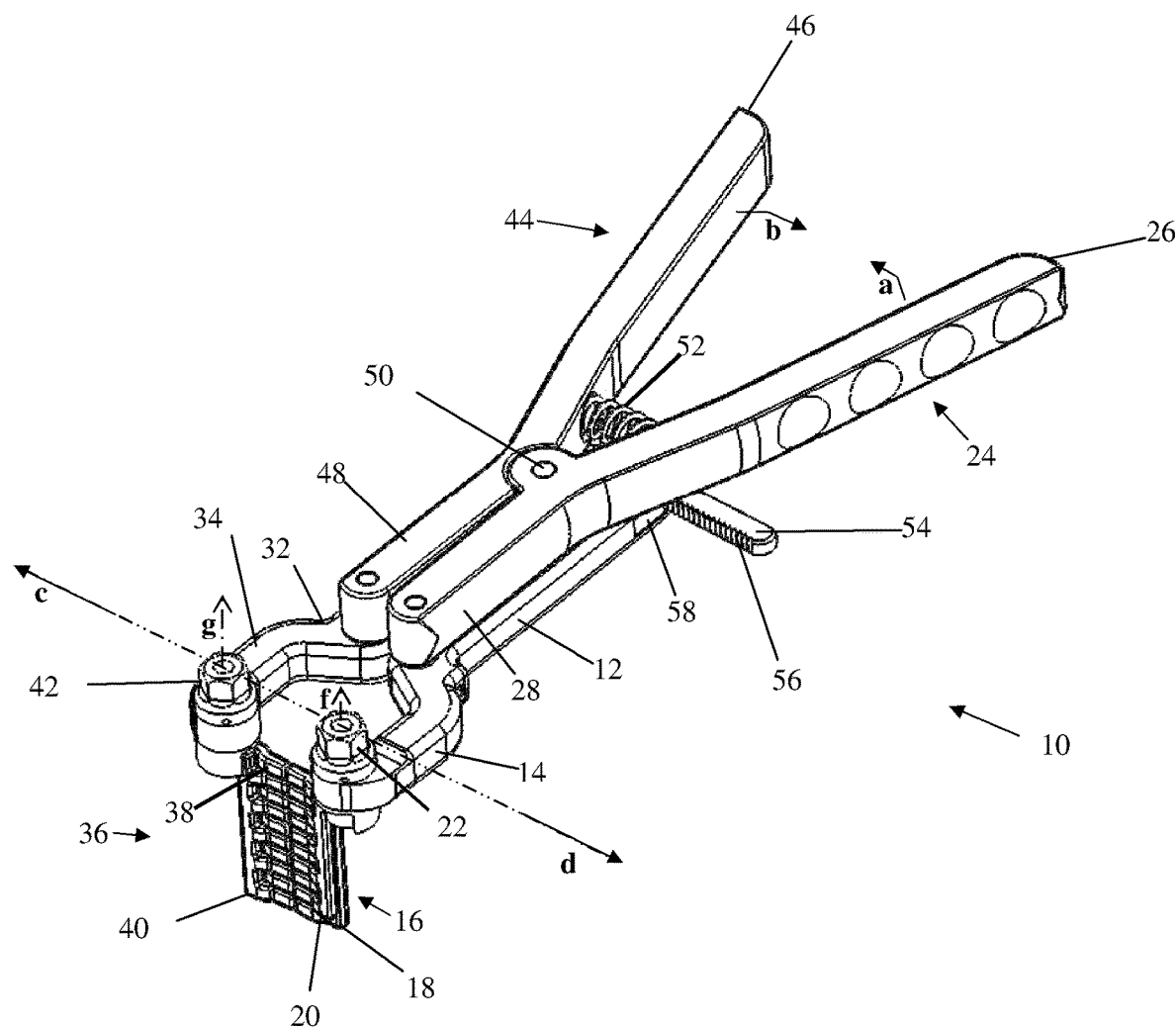
FIG. 1 provides a perspective view of a retractor with a pair of blade assemblies in a closed and parallel configuration.

The retractor embodiments described herein provides advantages over the prior art retractors comprising a set of blades and an actuator, such as a set of scissor arms. Additional details of these embodiments can be found in U.S. Pat. No. 8,142,355 (issued on Mar. 27, 2012), which is hereby incorporated in its entirety herein. The retractor embodiments described herein can allowed the person skilled in the art to insert a relatively compact set of retractor blades into an incision having a short length. In some embodiments, the compact set of retractor blades are of such a size that they can be inserted within the incision so that they are snugly embraced by the side walls of the incision. Activation of an actuator causes the blades to move apart in a direction that is essentially parallel to the length of the incision. This causes the tissue to stretch in one direction, creating an opening having a length in that direction that is substantially longer than the incision. Once the retractor is opened in the first direction, the actuator may be locked open. Then a pair of adjusters on the blade assemblies may be manipulated to open the blade assemblies, thus pulling the incised tissue apart in directions that are not parallel to the incision. In some embodiments, these directions may be perpendicular, substantially perpendicular or oblique to the incision. Thus there is opened up an aperture that is substantially longer than the incision, and thus is substantially larger than would be possible using a prior art device. Thus in relative terms, the surgeon may use a smaller incision, and in some cases a much smaller incision, than would have been required with a prior art device. Moreover, removal of the retractor, e.g. by closing the blade assemblies, replacing the handles (if necessary), closing the arm assembly and removing the blade assemblies from the incision, causes the incision to relax back to a size that is much smaller than would have resulted from use of the prior art retractor.

In some embodiments, the handles, the blade assemblies or both are removable. In some embodiments, the blades of the blade assemblies may take on a variety of shapes and sizes. In some embodiments, a kit can include a plurality of retractors having blades of various sizes, shapes or both. In some embodiments, the kit comprises one or more sets of handles, one or more arm assemblies and two or more blade assemblies (optionally of varying blade sizes and/or shapes). In some embodiments, a kit includes a retractor of as described herein optionally more than two blades, at least two of which differ from one another in size, shape or both, and one or more pedicle screws for performing lumbar surgery. Thus, the embodiments described herein provides a retractor, a variety of surgical kits for performing surgery, especially back surgery, and methods of using the retractor to perform surgery, and especially back surgery.

The foregoing and further needs are met by embodiments, which provide (a) a retractor comprising: (a) a first blade assembly comprising a first blade rotatable about a first axis, a second blade rotatable about said first axis and an adjuster in mechanical communication with the first and second blades and adapted to rotate the first and second blades relative to each other about said first axis; (b) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (c) a means for moving said first blade assembly relative to said second blade assembly along a third axis that is not parallel to said first and second axes. It is to be understood by one of ordinary skill in the art that, while at present a preferred embodiment uses a means for moving said first blade assembly relative to said second blade assembly employs two arms that are held parallel to one another by a means for stabilizing the arms, it is also possible for said means for moving said first blade assembly relative to said second blade assembly to be a pair of crossing arms joined to one another at a pivot point. In such cases, the blade assemblies move relative to one another along an arc. Nonetheless, their general direction of motion relative to one another, and the direction of motion that is of especial interest in the context of the present application, is along an axis that is generally defined by a line passing through the blade assemblies, e.g. at the point where each blade assembly is attached to its respective arm. In particular embodiments, the second blade assembly comprises a third blade, a fourth blade and an adjuster in mechanical communication with the third and fourth blades and adapted to rotate the third and fourth blades relative to each other about said second axis. In some such embodiments, the first and second axes may be substantially coplanar with one another. Indeed in some currently preferred embodiments, the first and second axes are not only coplanar but also substantially parallel to one another. In particular embodiments, the first and second axes are coplanar with, parallel to, or at some pre-determined skew angle with respect to one another. In some specific examples, the third axis is substantially perpendicular to the first axis, the second axis or both the first and second axes. In particular embodiments, the third axis is substantially perpendicular to both the first axis and the second axis. In some embodiments, the third axis is perpendicular to the first axis, the second axis or both the first and second axes. In some specific embodiments, the third axis is perpendicular to both the first and second axes. In some embodiments, the retractor described herein possesses a means for locking said first and second blade assemblies in at least one predetermined position along said second axis. In some particular embodiments, two of said blades are of substantially different sizes in at least one dimension. In some specific embodiments, at least two blades of different sizes form part of the same blade assembly, while in other embodiments, two blades of different sizes form parts of different blade assemblies. In some particular embodiments, at least one of the first, second, third and, when present, forth blades is a comb-shaped blade. In some embodiments, at least one of the first, second, third and, when present, fourth blades is a substantially flat blade. In some embodiments, Some embodiments include at least one removable blade assembly. In some specific embodiments, both blade assemblies are removable.

In some embodiments, a method (e.g. a method of surgery—in particular spinal surgery, e.g. in the lumbar region of the back) comprises the steps of: (a) providing a retractor comprising: (i) a first blade assembly comprising a first blade rotatable about a first axis, a second blade rotatable about said first axis and an adjuster in mechanical communication with the first and second blades and adapted to rotate the first and second blades relative to each other about said first axis; (ii) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (iii) a means for moving said first blade assembly relative to said second blade assembly along a third axis that is not parallel to said first and second axes; (b) adjusting the first and second blades of the first blade assembly to be substantially parallel to each other to form a first closed blade assembly; (c) adjusting the third blade, and when present the fourth blade, of the second blade assembly to be substantially parallel to the first and second blades of the first blade assembly; (d) making an incision in a tissue of a body; (e) inserting said first blade assembly and said second blade assembly within the incision; (f) moving the first blade assembly away from the second blade assembly along said third axis and along the length of the incision so that the incision is stretched to create an opening longer than the incision; and (g) adjusting the first and second blades of the first blade assembly about said first axis to an open position, and, when said fourth blade of said second blade assembly is present, adjusting the third and fourth blades of the second blade assembly substantially about said second axis to an open position, thereby stretching the incision out from said third axis and creating an aperture in the tissue that is longer and wider than the incision. In some such embodiments, the second blade assembly comprises a third blade, a fourth blade and an adjuster in mechanical communication with the third and fourth blades and adapted to rotate the third and fourth blades relative to each other about said second axis. In some particular embodiments, the first and second axes are substantially coplanar with one another, substantially parallel to one another and/or substantially perpendicular to the third axis. The third axis is the line passing through the points at which the blade assemblies are joined to the arms of the retractor. As mentioned above, the person skilled in the art will recognize that when the arms are scissor-like arms that cross one another and are joined at a pivot point, the motion of the blade assemblies with respect to one another will trace out an arc. However, the direction of motion of the two blade assemblies with respect to one another will be essentially along the third axis. In any case, in particular embodiments, the first and second axes are coplanar with one another, parallel to one another and/or perpendicular to the third axis. In particular embodiments, the third axis is perpendicular to the first axis, the second axis or both the first and second axes. In some particular embodiments, the third axis is perpendicular to both the first and second axes. In some embodiments, at least two of said blades are of substantially different sizes in at least one dimension (e.g. length, width or both). In some specific embodiments, said two blades of different sizes form part of the same blade assembly. In other specific embodiments, said two blades of different sizes form parts of different blade assemblies. In some embodiments, at least one of the first, second, third and, when present, fourth blades is a comb-shaped blade. In some embodiments, at least one of the first, second, third and, when present, fourth blades is a substantially flat blade. In some embodiments, the retractor further comprise a means for locking said first blade assembly and second blade assembly in a position apart from each other along said second axis. In some embodiments, the method further comprises removing at least a part of said means for moving the first and second blade assemblies toward and away from each other along the second axis. In some embodiments, the incision is made in the lumbar region of the back near the spine. In some embodiments, the method further comprises placing one or more pedicle screws in the spine of the body. In other embodiments, the method further comprises adjusting the first and second blade assemblies to closed positions and removing the retractor from the incision, thereby returning the incision to substantially the same shape and size as prior to retractor insertion. In still further embodiments, at least one blade assembly is removable. In specific embodiments, both blade assemblies are removable.

In some embodiments, a kit for performing an operation, includes: (a) a retractor comprising: (i) a first blade assembly comprising a first blade rotatable about a first axis, a second blade rotatable about said first axis and an adjuster in mechanical communication with the first and second blades and adapted to rotate the first and second blades relative to each other about said first axis; (ii) a second blade assembly comprising at least a third blade rotatable about a second axis and optionally a fourth blade rotatable about said second axis and, when said fourth blade is present in said second blade assembly, an adjuster in mechanical communication with the third and fourth blades and adapted to rotate the third and fourth blades relative to each other about said second axis, wherein said second axis is different from said first axis; and (iii) a means for moving said first blade assembly relative to said second blade assembly along a third axis that is not parallel to said first and second axes; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the second blade assembly of the retractor comprises a third blade, a fourth blade and an adjuster in mechanical communication with the third and fourth blades and adapted to rotate the third and fourth blades relative to each other about said second axis. In some embodiments, the first and second axes are substantially coplanar with one another. In specific embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In particular embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some specific embodiments, both blade assemblies are removable.

In some embodiments, a retractor comprises: (a) a first arm having a distal end and a proximal end; (b) a second arm having a distal end and a proximal end; (c) a first blade assembly, attached near the distal end of the first arm and comprising a first blade, a second blade and an adjuster in mechanical communication with the first and second blades and adapted to rotate the first and second blades relative to each other about a first axis; (d) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (e) an actuator adapted to move at least the distal ends of said first and second arms relative to each other along a third axis that is not parallel to the first and second axes. In some embodiments of the retractor, the second blade assembly comprises a third blade, a fourth blade and an adjuster in mechanical communication with the third and fourth blades and adapted to rotate the third and fourth blades relative to each other about said second axis. In some embodiments, the first and second axes are substantially coplanar with one another. In some embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, at least two of said blades are of substantially different sizes in at least one dimension (e.g. length, width or both). In some embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the actuator comprises a stabilizer which maintains at least a portion of each of the first and second arms in an attitude substantially parallel to each other when the first and second arms are moved toward and away from each other. In some embodiments, the stabilizing member comprises a first crosspiece having first and second ends, a second crosspiece having third and fourth ends, the first and second crosspieces being connected to each other by a pivot, the first end of the first crosspiece being connected to the first arm by a pivot, the second end of the first crosspiece being slidably connected to the second arm, the third end of the second crosspiece being connected to the second arm by a pivot and the fourth end of the second crosspiece being slidably connected to the first arm. In some specific embodiments, the first end of the first crosspiece is connected to the first arm at a position distal to the slidable connection of the fourth end of the second crosspiece to the first arm. In some more specific embodiments, the third end of the second crosspiece is connected to the second arm at a position distal to the slidable connection of the second end of the first crosspiece to the second arm. In some embodiments, the retractor further comprises a lock adapted to reversibly hold said first and second arms apart from each other along the second axis. In some specific embodiments, the lock is a ratchet lock comprising a ratchet blade and a ratchet release. In some more specific embodiments, the ratchet lock holds the first arm and the second arm apart from each other along the second axis. In some embodiments, the actuator comprises a first handle connected to the proximal end of the first arm and a second handle connected to the proximal end of the second handle, wherein the first handle and the second handle are adapted to move the distal ends of the first and second arms toward and away from each other along the second axis. In some specific embodiments, the first and second handles are connected by a pivot. In some additional embodiments, the actuator further comprises a biasing member adapted to bias the actuator toward a preselected condition. In some specific embodiments, the biasing member is a biasing spring. In some embodiments, the biasing spring biases the distal ends of the first and second arms toward each other.

In some embodiments, a method (e.g. a surgical method for surgery on the spine, e.g. the lumbar region of the spine) includes the steps of: (a) providing a retractor comprising: (i) a first arm having a distal end and a proximal end; (ii) a second arm having a distal end and a proximal end; (iii) a first blade assembly, attached near the distal end of the first arm and comprising a first blade, a second blade and an adjuster in mechanical communication with the first and second blades and adapted to rotate the first and second blades relative to each other about a first axis; (iv) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (v) an actuator adapted to move at least the distal ends of said first and second arms relative to each other along a third axis that is not parallel to the first and second axes; (b) ensuring that the first and second blades of the first blade assembly are substantially parallel to each other to form a first closed blade assembly; (c) ensuring that the third blade, and when present the fourth blade, of the second blade assembly are substantially parallel to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision. In some embodiments, the method optionally comprises adjusting the third and fourth blades of the second blade assembly to an open position. In some embodiments, the actuator comprises a means for locking the first and second arms in a position apart from each other along the second axis, wherein the method further comprises locking said first and second arms in a position apart from each other along the second axis. In some embodiments, the actuator further comprises a set of removable handles, the method optionally further comprising removing said set of removable handles from the first and second arms. In other embodiments, the incision is made in the lumbar region of the back near the spine. In further embodiments, the method further comprises placing one or more pedicle screws in the spine of the body. In some embodiments the method further comprises closing the first and second blade assemblies and removing the retractor from the incision, thereby returning the incision to substantially the same shape and size as prior to retractor insertion.

In some embodiments, a kit (e.g. a surgical kit, especially a spinal surgery kit, and most particularly a spinal surgery kit for surgery on the lumbar region of the spine. In some embodiments, the kit comprises: (a) a retractor comprising: (i) a first arm having a distal end and a proximal end; (ii) a second arm having a distal end and a proximal end; (iii) a first blade assembly, attached near the distal end of the first arm and comprising a first blade, a second blade and an adjuster in mechanical communication with the first and second blades and adapted to rotate the first and second blades relative to each other about a first axis; (iv) a second blade assembly attached near the distal end of the second arm and comprising at least a third blade rotatable about a second axis, optionally a fourth blade, and when the fourth blade is present, an adjuster in mechanical communication with the third and fourth blades and adapted to rotate the third and fourth blades relative to each other about said second axis; and (v) an actuator adapted to move at least the distal ends of said first and second arms relative to each other along a third axis that is not parallel to the first and second axes; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the second blade assembly comprises a third blade, a fourth blade and an adjuster in mechanical communication with the third and fourth blades and adapted to rotate the third and fourth blades relative to each other about said second axis. In some embodiments, the first and second axes are substantially coplanar with one another. In some embodiments, the first and second axes are coplanar with one another. In some embodiments, the third axis is substantially perpendicular to the first axis, the second axis or both the first and second axes. In some specific embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In some embodiments, at least two blades of different sizes form part of the same blade assembly. In some specific embodiments, two blades of different sizes form parts of different blade assemblies. In some other embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some specific embodiments, both blade assemblies are removable. In some embodiments, the actuator comprises a stabilizer which maintains at least a portion of each of the first and second arms in an attitude substantially parallel to each other when the first and second arms are moved toward and away from each other. In some specific embodiments, the stabilizing member comprises a first crosspiece having first and second ends, a second crosspiece having third and fourth ends, the first and second crosspieces being connected to each other by a pivot, the first end of the first crosspiece being connected to the first arm by a pivot, the second end of the first crosspiece being slidably connected to the second arm, the third end of the second crosspiece being connected to the second arm by a pivot and the fourth end of the second crosspiece being slidably connected to the first arm. In some embodiments, the first end of the first crosspiece is connected to the first arm at a position distal to the slidable connection of the fourth end of the second crosspiece to the first arm. In some embodiments, the third end of the second crosspiece is connected to the second arm at a position distal to the slidable connection of the second end of the first crosspiece to the second arm. In some embodiments, the retractor further comprises a lock adapted to reversibly hold said first and second arms apart from each other along the second axis. In some specific embodiments, the lock is a ratchet lock comprising a ratchet blade and a ratchet release. In some more specific embodiments, the ratchet lock holds the first arm and the second arm apart from each other along the second axis. In some embodiments, the actuator comprises a first handle connected to the proximal end of the first arm and a second handle connected to the proximal end of the second handle, wherein the first handle and the second handle are adapted to move the distal ends of the first and second arms toward and away from each other along the second axis. In some embodiments, the first and second handles are connected by a pivot. In some embodiments, the actuator further comprises a biasing member adapted to bias the actuator toward a preselected condition. In some embodiments, the biasing member is a biasing spring. in some specific embodiments, the biasing spring biases the distal ends of the first and second arms toward each other.

In some embodiments, a retractor includes: (a) a first arm having a distal end and a proximal end; (b) a second arm having a distal end and a proximal end, at least said distal end of said first arm and said distal end of said second arm being movable toward and away from each other; (c) a first blade assembly attached near the distal end of the first arm, which comprises a first blade, a second blade and a means for moving said first and second blades relative to each other about a first axis to adopt at least an opened position and a closed position; (d) a second blade assembly attached near the distal end of the second arm, which comprises a third blade, a fourth blade and a means for moving said third and fourth blades relative to each other about a second axis different from said first axis; and (e) a means for moving at least said distal end of said first arm and said distal end of said second arm relative to one another along a third axis that is not parallel to said first and second axes. In some embodiments, the first and second axes are substantially coplanar with one another. In some specific embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some specific embodiments, the third axis is perpendicular to both the first and second axes. In some embodiments, the retractor further comprises a means for locking said first and second blade assemblies in at least one predetermined position along said second axis. In some embodiments, two of said blades are of substantially different sizes in at least one dimension. In some embodiments, two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the means for moving at least said distal end of said first arm and said distal end of said second arm relative to one another along the second axis comprises a means for maintaining at least a portion of each of the first and second arms in an attitude substantially parallel to each other when the first and second arms are moved toward and away from each other. In some embodiments, the retractor further comprises a means for locking the first and second arms in at least one preselected position. In some embodiments, the means for moving at least said distal end of said first arm and said distal end of said second arm toward along said third axis comprises a removable means for moving said first arm and said second arm relative to each other along the second axis. In some embodiments, the removable means for moving said first arm and said second arm toward and away from each other further comprises a means for biasing the arms toward or away from each other.

In some embodiments, a method (e.g. a method of surgery, such as spinal surgery, and in particular spinal surgery in the lumbar region of the back) includes the steps of: (a) providing a retractor comprising: (i) a first arm having a distal end and a proximal end; (ii) a second arm having a distal end and a proximal end, at least said distal end of said second arm and said distal end of said second arm being movable toward and away from each other; (iii) a first blade assembly attached near the distal end of the first arm, which comprises a first blade, a second blade and a means for moving said first and second blades relative to each other along a first axis to adopt at least an opened position and a closed position; (iv) a second blade assembly attached near the distal end of the second arm, which comprises a third blade, a fourth blade and a means for moving said third and fourth blades relative to each other substantially along the first axis to adopt at least an opened position and a closed position; and (v) a means for moving at least said distal end of said first arm and said distal end of said second arm relative to one another along a second axis; (b) ensuring that the first and second blades of the first blade assembly are substantially parallel to each other; (c) ensuring that the third and fourth blades of the second blade assembly are substantially parallel to each other and to the first and second blades of the first blade assembly; (d) making an incision in a tissue of a body; (e) inserting said first blade assembly and said second blade assembly within the incision; (f) actuating the retractor such that said first blade assembly and second blade assembly are moved apart from one another along the second axis and the incision is stretched along the length of the incision to create an opening longer than the incision; and (g) adjusting the first and second blades of the first blade assembly along said first axis to an open position, and, when said fourth blade of said second blade assembly is present, adjusting the third and fourth blades of the second blade assembly substantially along said second axis to an open position, thereby stretching the incision along the first axis and creating an aperture in the tissue that is longer and wider than the incision. In some embodiments, the actuator comprises a means for locking the first and second arms in a position apart from each other along the second axis, the method optionally further comprising locking said first and second arms in a position apart from each other. In some embodiments, the actuator further comprises a set of removable handles, optionally further comprising removing said set of removable handles from the first and second arms. In some embodiments, the incision is made in the lumbar region of the back near the spine. In some embodiments, the method further comprises placing one or more pedicle screws in the spine of the body. In some embodiments, the method further comprises closing the first and second blade assemblies and removing the retractor from the incision, thereby returning the incision to substantially the same shape and size as prior to retractor insertion.

The in some arrangements a kit can include (a) a retractor comprising: (i) a first arm having a distal end and a proximal end; (ii) a second arm having a distal end and a proximal end, at least said distal end of said first arm and said distal end of said second arm being movable toward and away from each other; (iii) a first blade assembly attached near the distal end of the first arm, which comprises a first blade, a second blade and a means for moving said first and second blades relative to each other along a first axis to adopt at least an opened position and a closed position; (iv) a second blade assembly attached near the distal end of the second arm, which comprises a third blade, a fourth blade and a means for moving said third and fourth blades relative to each other substantially along the first axis to adopt at least an opened position and a closed position; and (v) a means for moving at least said distal end of said first arm and said distal end of said second arm relative to one another along a second axis; and (b) at least one member of the group consisting of instructions for using the retractor to perform a surgical operation, scalpels, suture needles, pedicle screws, suture material, spinal implant material, spinal fusion rods, biocompatible adhesive and closure staples. In some embodiments, the first and second axes are substantially coplanar with one another. In some embodiments, the first and second axes are coplanar with one another. In some embodiments, the third axis is substantially perpendicular to the first axis, the second axis or both the first and second axes. In some embodiments, the third axis is substantially perpendicular to both the first axis and the second axis. In some embodiments, the third axis is perpendicular to the first axis, the second axis or both the first and second axes. In some embodiments, the third axis is perpendicular to both the first and second axes. In some embodiments, the retractor of the kit further comprises a means for locking said first and second blade assemblies in at least one predetermined position along said second axis. In some embodiments, at least two of said blades are of substantially different sizes in at least one dimension. In some embodiments, at least two blades of different sizes form part of the same blade assembly. In some embodiments, two blades of different sizes form parts of different blade assemblies. In some embodiments, at least one of the first, second, third and, when present, forth blades is a comb-shaped blade. In some embodiments, at least one of the first, second, third and, when present, fourth blades is a substantially flat blade. In some embodiments, at least one blade assembly is removable. In some embodiments, both blade assemblies are removable. In some embodiments, the means for moving at least said distal end of said first arm and said distal end of said second arm relative to one another along the second axis comprises a means for maintaining at least a portion of each of the first and second arms in an attitude substantially parallel to each other when the first and second arms are moved toward and away from each other. In some embodiments, the retractor of the kit further comprises a means for locking the first and second arms in at least one preselected position. In some embodiments, the means for moving at least said distal end of said first arm and said distal end of said second arm toward along said third axis comprises a removable means for moving said first arm and said second arm relative to each other along the second axis. In some embodiments, the removable means for moving said first arm and said second arm toward and away from each other further comprises a means for biasing the arms toward or away from each other.

In some embodiments, a retractor blade assembly, includes: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope, (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions. In some embodiments of the blade assembly the third angle is opposite in sign and congruent with the first angle and the fourth angle is opposite in sign and congruent with the second angle. In some embodiments of the blade assembly at least the first angle has a magnitude with respect to the axis of less than about 75.degree. In some embodiments of the blade assembly, each angle has a magnitude with respect to the axis of less than about 75.degree. In some embodiments of the blade assembly each angle has a magnitude with respect to the axis of about 20.degree. to about 70.degree. In some embodiments of the blade assembly, each channel has a first end and a second end and the nut and plunger are threaded so that the rod moves from the first end of the channels to the second end within 1 to 10 full rotations of the nut. In some embodiments of the blade assembly, the rod moves from the first end to the second end of the channels within 2 to 8 full rotations of the nut. In some embodiments of the blade assembly the rod moves from the first end to the second end of the channels within 3 to 6 full rotations of the nut. In some embodiments of the blade assembly, the rod moves from the first end to the second end of the channels within 4 to 6 full rotations of the nut. In some embodiments of the blade assembly, at least one blade is comb shaped. In some embodiments of the blade assembly, both blades are comb shaped. In some embodiments of the blade assembly, at least one blade is fan shaped. In some embodiments of the blade assembly, both blades are comb shaped. In some embodiments of the blade assembly, the holder is adapted to be removably affixed to an arm of a retractor. In some embodiments of the blade assembly, the holder is irreversibly affixed to an arm of a retractor.

Thus, the some embodiments provides a retractor as described herein, wherein at least one blade assembly is a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope, (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions. In some embodiments, the third angle is opposite in sign and congruent with the first angle and the fourth angle is opposite in sign and congruent with the second angle. In some embodiments, at least the first angle has a magnitude with respect to the axis of less than about 75.degree. In some embodiments, each angle has a magnitude with respect to the axis of less than about 75.degree. In some embodiments, each angle has a magnitude with respect to the axis of about 20.degree. to about 70.degree. In some embodiments, each channel has a first end and a second end and the nut and plunger are threaded so that the rod moves from the first end of the channels to the second end within 1 to 10 full rotations of the nut. In some embodiments, the rod moves from the first end to the second end of the channels within 2 to 8 full rotations of the nut. In some embodiments, the rod moves from the first end to the second end of the channels within 3 to 6 full rotations of the nut. In some embodiments, the rod moves from the first end to the second end of the channels within 4 to 6 full rotations of the nut. In some embodiments, at least one blade is comb shaped. In some embodiments, both blades are comb shaped. In some embodiments, at least one blade is fan shaped. In some embodiments, both blades are comb shaped. In some embodiments, the holder is adapted to be removably affixed to an arm of a retractor. In some embodiments the holder is irreversibly affixed to an arm of a retractor.

In some embodiments, a kit includes a retractor as described herein, wherein at least one blade assembly comprises: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope; (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions.

In some embodiments, a method as described herein uses a retractor as described herein, wherein at least one blade assembly is a retractor blade assembly, comprising: (a) a first blade having attached thereto a first barrel, the first barrel having a wall circling an axis and defining a first lumen, a first channel in the wall having a first slope with respect to the axis and a second channel in the wall having a second slope with respect to the axis and having C2 symmetry about the axis with respect to the first slope; (b) a second blade having attached thereto a second barrel, the second barrel having a wall circling an axis and defining a second lumen, a third channel in the second wall having a third slope at a third angle with respect to the axis, and a fourth channel in the second wall having a fourth slope at a fourth angle with respect to the axis, the slope of the third angle being opposite in sign with respect to the axis to that of the first angle and the fourth channel having C2 symmetry about the axis with respect to the third channel, wherein the first barrel fits within the second lumen of the second barrel such that the first and third channels intersect to form a first gap and the second an fourth channels intersect to form a second gap; (c) a cylindrical plunger having an axis, an outer surface, a first end and a second end, the first end having a hole through and at a right angle to the plunger axis, and the second end having a screw thread cut into the surface of the plunger, the cylindrical plunger fitting within the first lumen of the first barrel such that said hole aligns with the first gap and the second gap and the hole, first gap and second gap forming a passage; (d) a rod fitting through the passage such that movement of the plunger along the axis causes the first barrel to rotate in a first direction and the second barrel to rotate in a second direction opposite the first direction; (e) a holder possessing a third lumen, wherein the second barrel fits within the third lumen; and (f) a nut having an internal screw thread and fitting over the end of the plunger; whereby rotation of the nut causes the internal screw thread of the nut to engage the plunger screw thread and causes the plunger to move along its axis, thereby causing the first and second barrels to rotate about the axis in opposite directions.

The embodiments will now be further described with reference to the appended drawings. In FIG. 1 there is shown a perspective view of a retractor 10 according to the present invention. The retractor 10 comprises a first arm 12, having a distal end 14 to which is attached a first blade assembly 16, comprising a first blade 18, a second blade 20 and an adjuster 22; a second arm 32, having a distal end 34, to which is attached a second blade assembly 36 comprising a third blade 38, a fourth blade 40 and an adjuster 42. The retractor further comprises a first handle 24 having a distal end 28 and a proximal end 26 and a second handle 44 comprising a distal end 48 and a proximal end 46. The two handles 24 and 44 are joined to one another by a pivot 50 and are spanned by a biasing spring 52. The retractor 10 further comprises a ratchet lock 54, which has serrations 56 that are adapted to engage an engagement member 58, which together with the ratchet lock 54 serves to hold the retractor in a particular position. In FIG. 1, the retractor 10 is shown in the "closed" position, meaning that the two blade assemblies 16 and 36 are relatively close to one another, as are the two arms 12 and 32 and the distal ends 28 and 48 of the handles 24 and 44, respectively. Depression of the proximal ends 26 and 46 of handles 24 and 44, respectively, in the directions of the arrows a and b results in the blade assemblies 16 and 36 moving apart along the directional arrows c and d, thus causing retractor 10 to assume the configuration depicted in FIG. 2. Note that the directional arrows c and d define a geometric line passing through and joining axis f, which passes vertically through first adjuster 22, and axis g, which passes vertically through second adjuster 42. Hereinafter axis f may be referred to alternatively as a first axis, axis g may be referred to alternatively as a second axis and the axis defined by directional arrows c and d may alternatively be referred to as a third axis. The importance of these axes will become evident upon consideration of the remaining figures.

Figure 2:
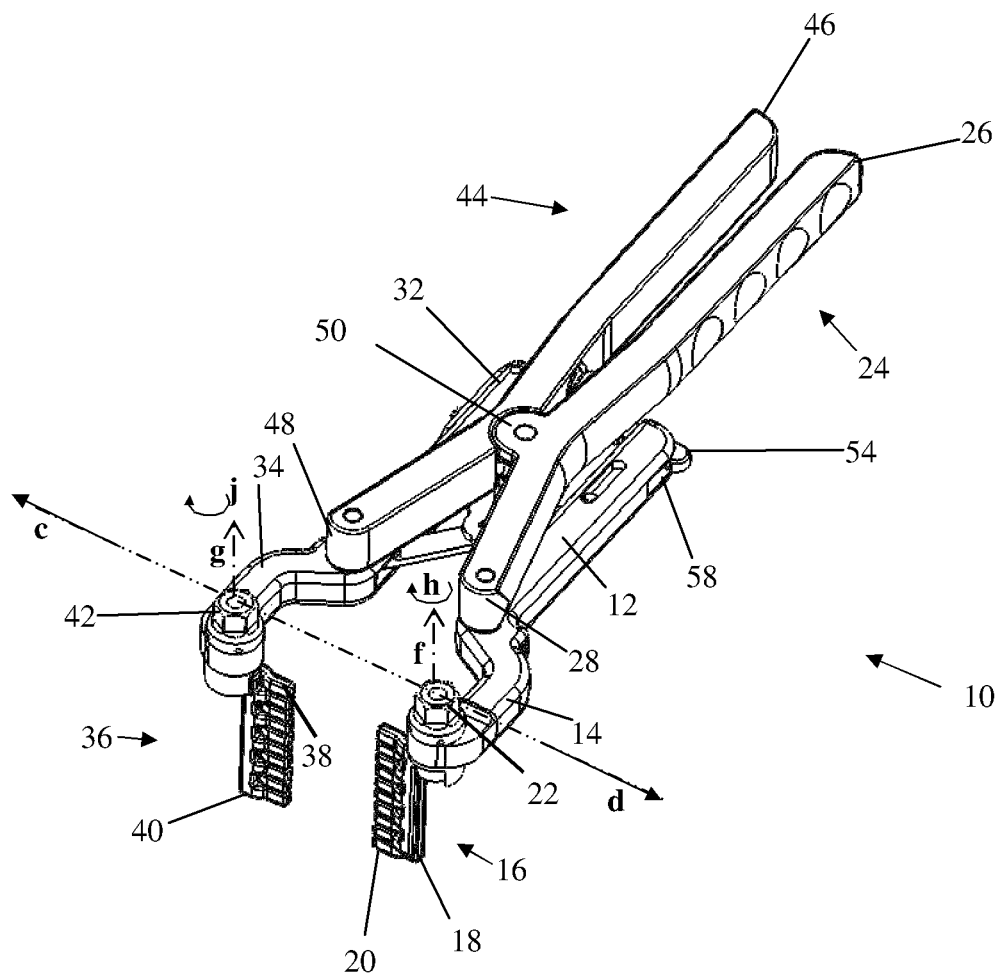
FIG. 2 provides a perspective view of a retractor, this time with the blades open in one direction along directional arrows c and d. Opening the retractor in this direction stretches the incision along its length.

As can be seen in FIG. 2, the retractor 10 is in an "open" position, meaning that the first blade assembly 16 is relatively separated from the second blade assembly 36 along the third axis defined by directional arrows c and d. Thus, as the blade assembly 16 moves along line d and blade assembly 36 moves along line c they exert force in the direction of lines d and c, respectively. Insertion of the blade assemblies 16 and 36 into an incision (not shown) in a closed position (as in FIG. 1) and opening the blade assemblies 16 and 36 to an open position (as in FIG. 2) results in a stretching of the incision along the same axis defined by directional lines c and d.

It is noted that in the embodiment depicted in FIGS. 1 and 2, the actuator comprises a pair of arms 12 and 32 and a pair of handles 24 and 44. The person skilled in the art will recognize that other embodiments of an actuator may be used. For example, scissor-like actuators are known in the clamp and retractor arts. In some such embodiments, the actuator comprises a pair of handles such as those depicted in FIG. 1 having attached at the distal ends of the handles 28 and 48 a pair of blade assemblies 16 and 36 according to the illustrated embodiment. Moreover, while the handles 24 and 44 are depicted as being roughly parallel and joined together at a pivot point 50, it is also within the skill in the art to use a pair of crossed (e.g. scissor-like) handles joined by a pivot. These and other embodiments of actuators are known in the art and contemplated as being within the scope of some aspects of the application. It is also to be understood that when the actuator is a scissor-like embodiment, the motion of blade assemblies 16 and 36 traverse an arc rather than a straight line upon opening of the retractor. Nevertheless, the spatial relationship of the two blade assemblies 16 and 36 can be conceptualized as changing along a line described by arrows c and d, which for the purpose of brevity is referred to herein as an axis, and in particular the third axis (axes f and g being the first and second axes).

Figure 7:
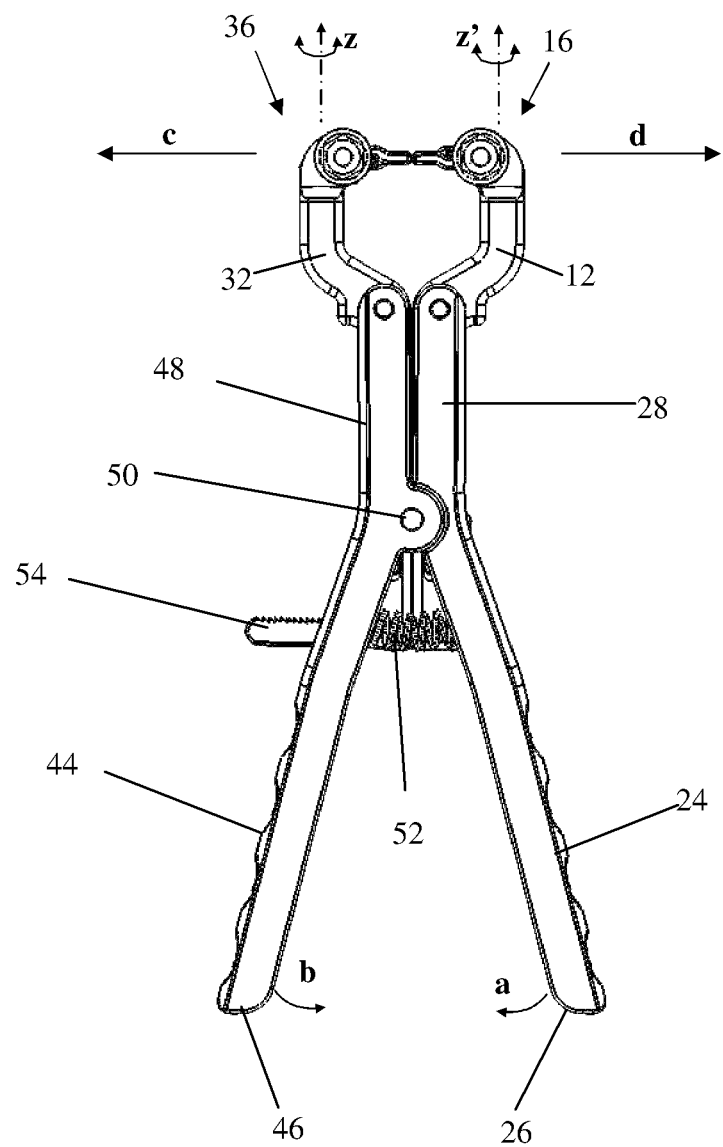
FIGS. 7, 8 and 9 provide top views of the retractor.
Figure 8:
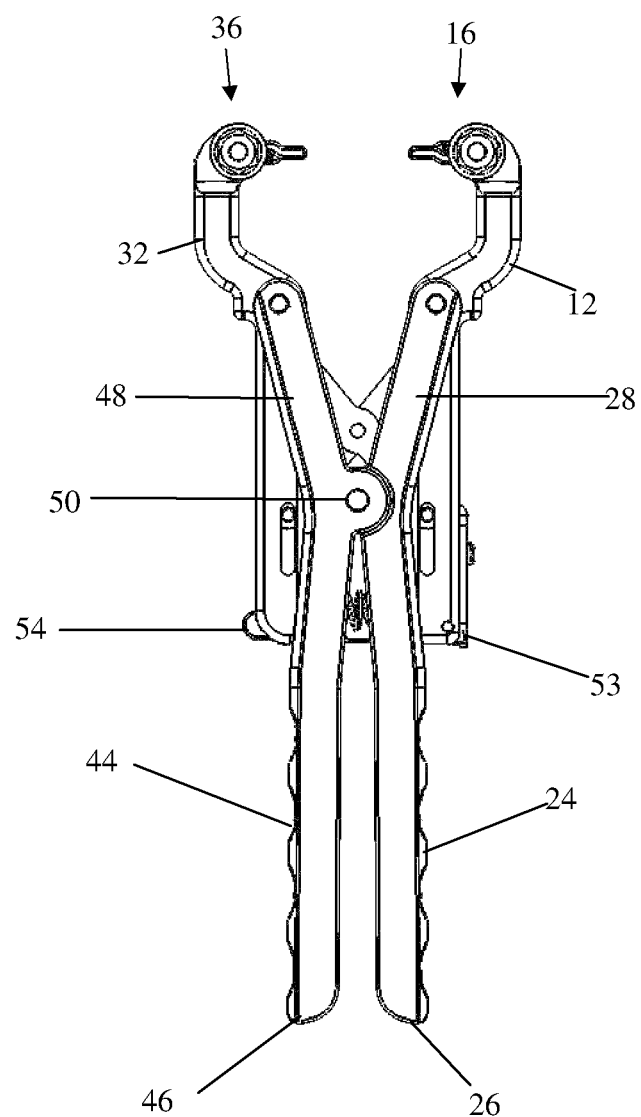

The actuator comprising a pair of arms 12 and 32 and a pair of handles 24 and 44 as just described allows movement of both arms 12 and 32 about pivot 50 (as illustrated in FIGS. 7 and 8). In some embodiments, the movement of one handle 24 toward the other handle 44 causes outward movement of only one arm while the other arm is left entirely fixed or moves a lessor amount. A retractor 10 system in which actuation of the system induces movement of only one arm (or reduced movement) of the retractor 10 can be particularly desirable in situations in which the retractor 10 will be used in close proximity to a delicate or sensitive anatomy. For example, if a surgeon desires to operate near a crucial nerve, the surgeon can use a retractor 10 with only one movable arm to protect the nerve by placing the fixed arm next to the nerve. Therefore, upon actuating the retractor 10, only the arm opposite the nerve will move out to open the surgery site. In such a manner, the surgeon can effectively protect crucial structures while using the retractor 10 herein disclosed to access a nearby surgery site. In operation, the retractor 10 with a fixed arm operated substantially the same as other embodiments of the retractors 10 herein disclosed. For example, both systems can have blade systems 36 and 16 to further expand the surgery site. Thus, in one arrangement, the retractor can include a said first blade assembly that movable relative to a fixed second blade assembly and wherein said first blade assembly is configured to detachably separate from said second blade assembly when said retractor is in an open configuration.

Figure 3:
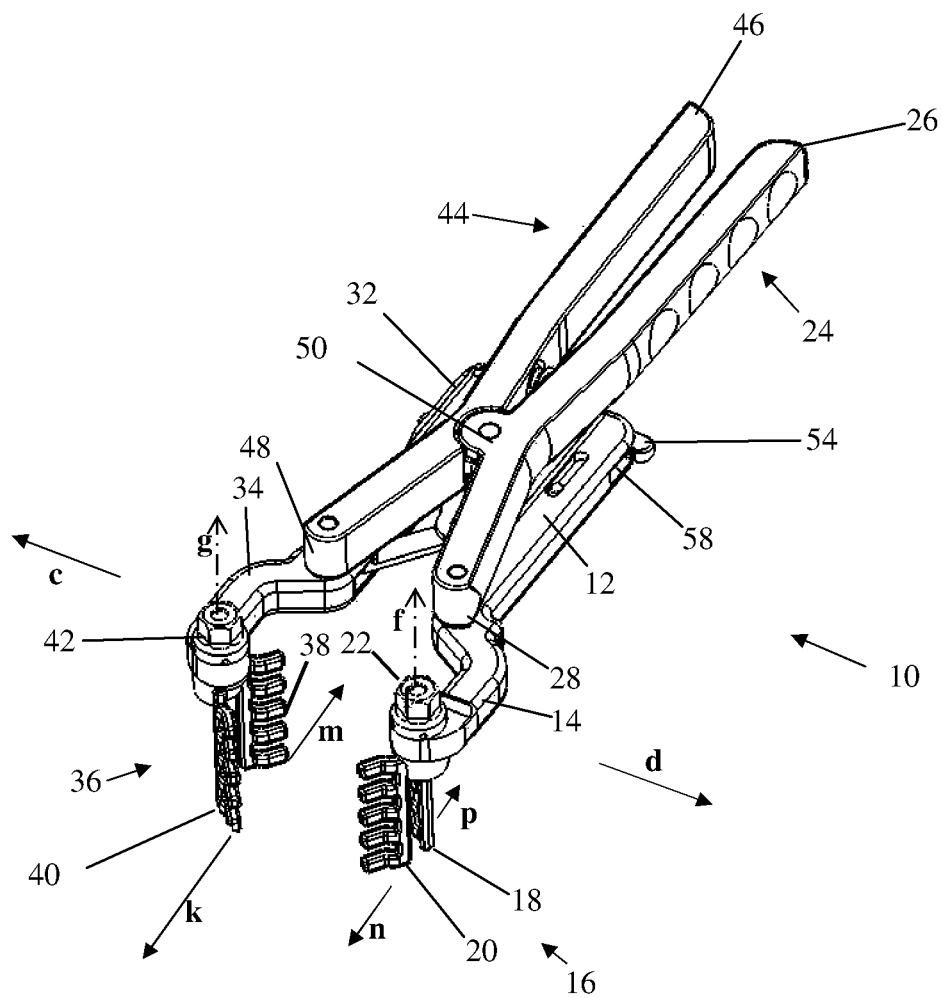
FIG. 3 provides a perspective view of a retractor, now with the two blade assemblies open in separate directions from the first direction of opening. Opening the retractor blade assemblies stretches the incision open in a second direction that is different from, and essentially not parallel to, the first direction.

Turning adjuster 22 about axis f in the direction of adjustment arrow h, and adjuster 42 about axis g in the direction of adjustment arrow j, results in opening of the blade assemblies 16 and 36, respectively, as depicted in FIG. 3. As shown in FIG. 3, opening of the blade assembly 16 causes the blade 20 to exert force in the direction of direction arrow n, while blade 18 exerts force in the direction of direction arrow p. Likewise, opening of blade assembly 36 causes blade 40 to exert force in the direction of arrow k, while blade 38 exerts force in the direction of arrow m. Thus, after insertion of the closed blade assemblies 16 and 36 of a closed retractor 10 in an incision, opening the retractor 10 and then opening the blade assemblies 16 and 36, the retractor 10 creates and maintains an aperture in the incised tissue that is both longer (i.e. dimensionally larger in the direction of the incision) and wider (i.e. dimensionally larger in a direction perpendicular or oblique to the direction of the incision) than the incision. It is to be understood that, while this description is especially apt where the incision is a straight line incision of about 0.1 to about 3 inches in length, it can apply to any shape of incision (e.g. an arc, a sinusoid, etc.) of any length. In particular embodiments of the appl- ciation, the contemplated size of the incision is about 0.5 to 2 inches in length and the blade assemblies 16 and 36 are appropriately sized so that when the retractor 10 is closed the blade assemblies 16 and 36 fit lengthwise within the incision without requiring substantial stretching of the incised tissue prior to opening of the retractor 10. Thus, in some embodi- ments, the blades 18, 20, 38 and 40 are sized to snugly fit within the incision when the blade assemblies are closed and the retractor is in a closed position.

Figure 4:
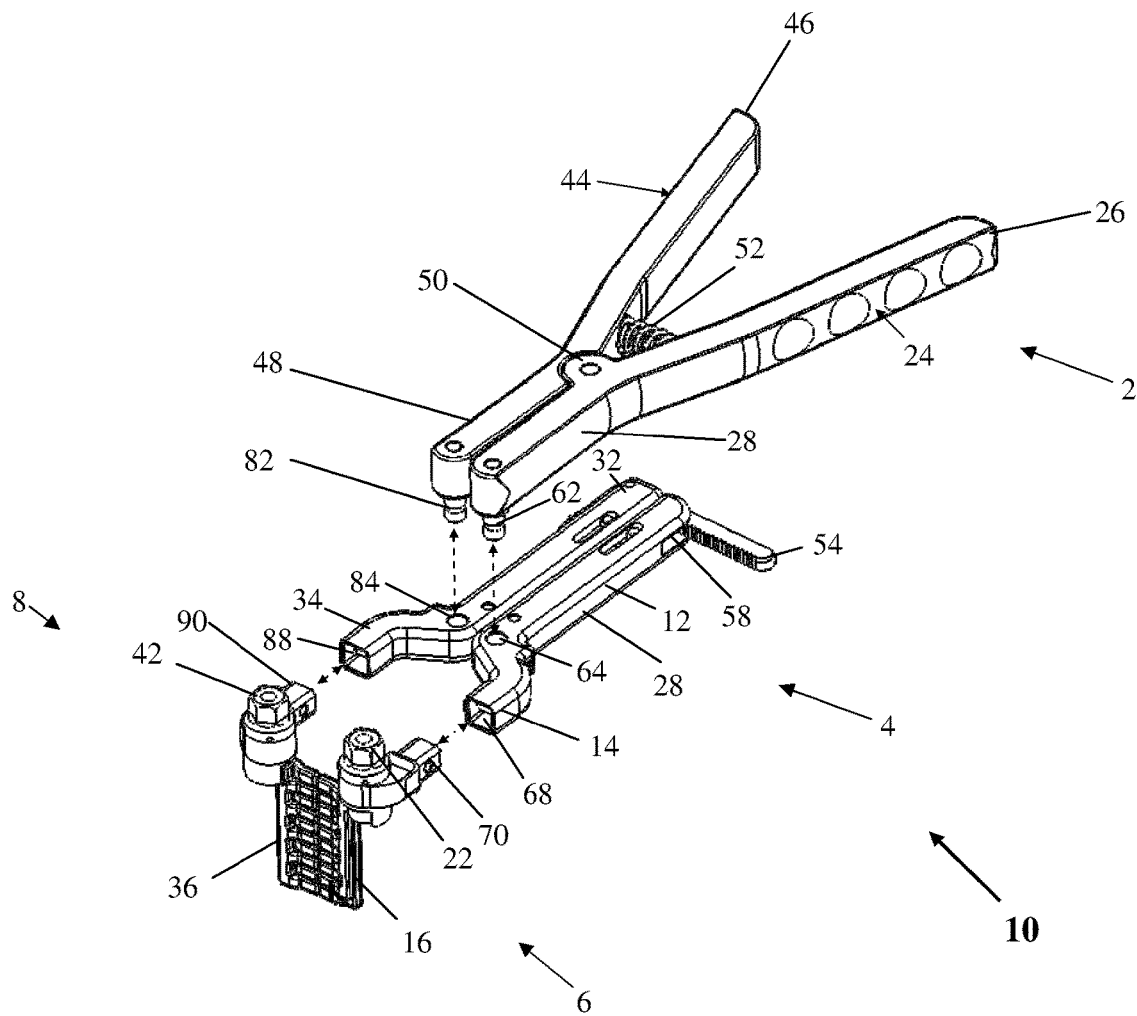
FIGS. 4, 5 and 6 provide exploded perspective views of a retractor, the handles being separated from the arm assembly and the blade assemblies being separated from the arm assembly.

FIG. 4 shows the device 10 with handle assembly 2, comprising inter alia the handles 24 and 44, separated from arm assembly 4, comprising inter alia arms 12 and 32. As can be seen in FIG. 4, the distal end 28 of handle 24 has a connecting pin 62 that fits within a connecting hole 64 on the first arm 12, while the distal end 48 of handle 44 has a connecting pin 82 that fits within a connecting hole 84 in the arm 32. In the depicted embodiment, the blade assembly 16 is removable from the distal end 14 of arm 12 and the blade assembly 36 is removable from the distal end 34 of arm 32. As depicted, the blade assembly 16 can be connected to the arm 12 by inserting the projection 70 on the proximal end of holder 6 within orifice 68 in the distal end 14 of arm 12. Likewise blade assembly 36 can be connected to arm 32 by inserting the projection 90 on the proximal end of holder 8 within the orifice 88 in the distal end 34 of arm 32.

Figure 5:
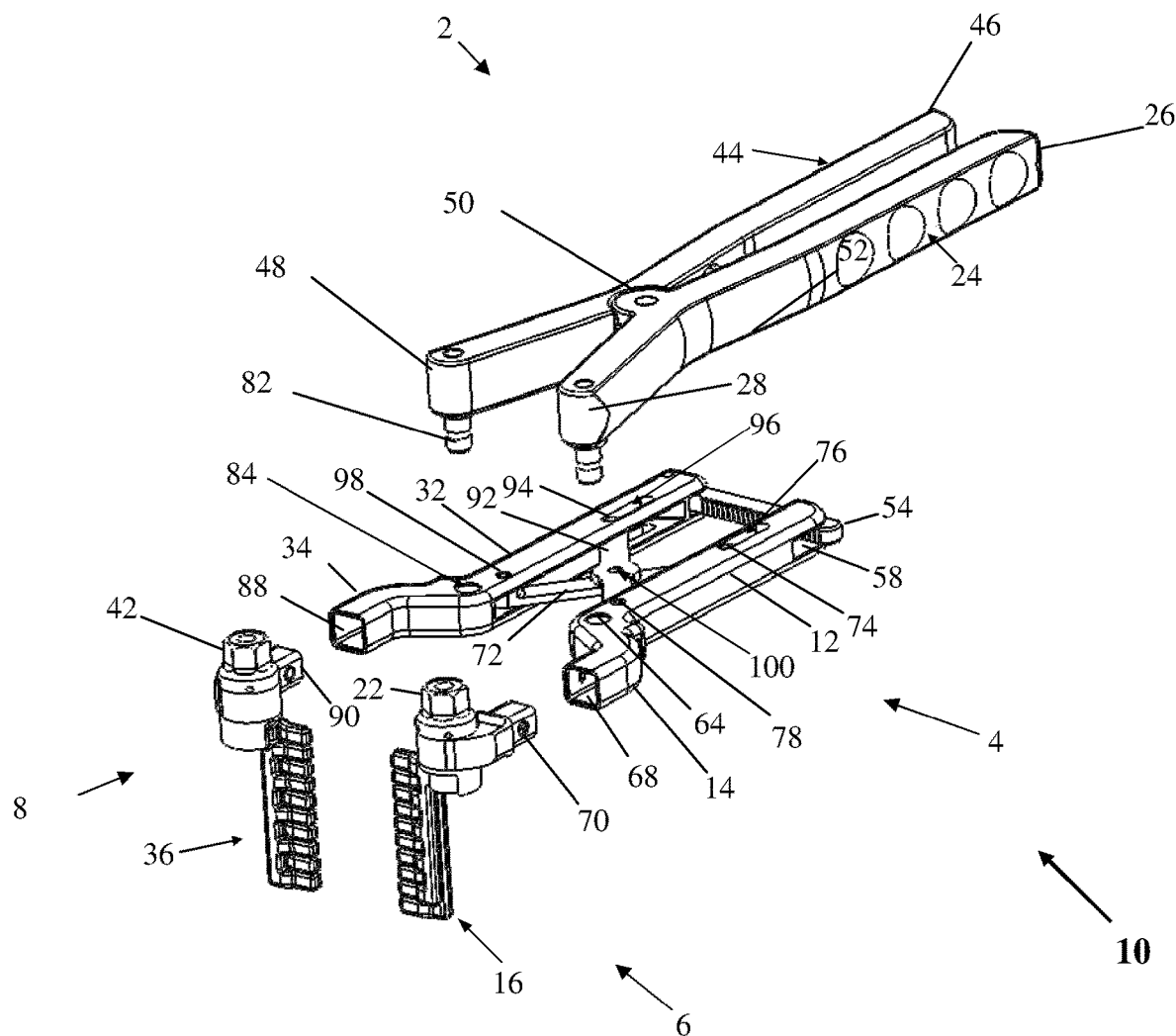
Figure 12:
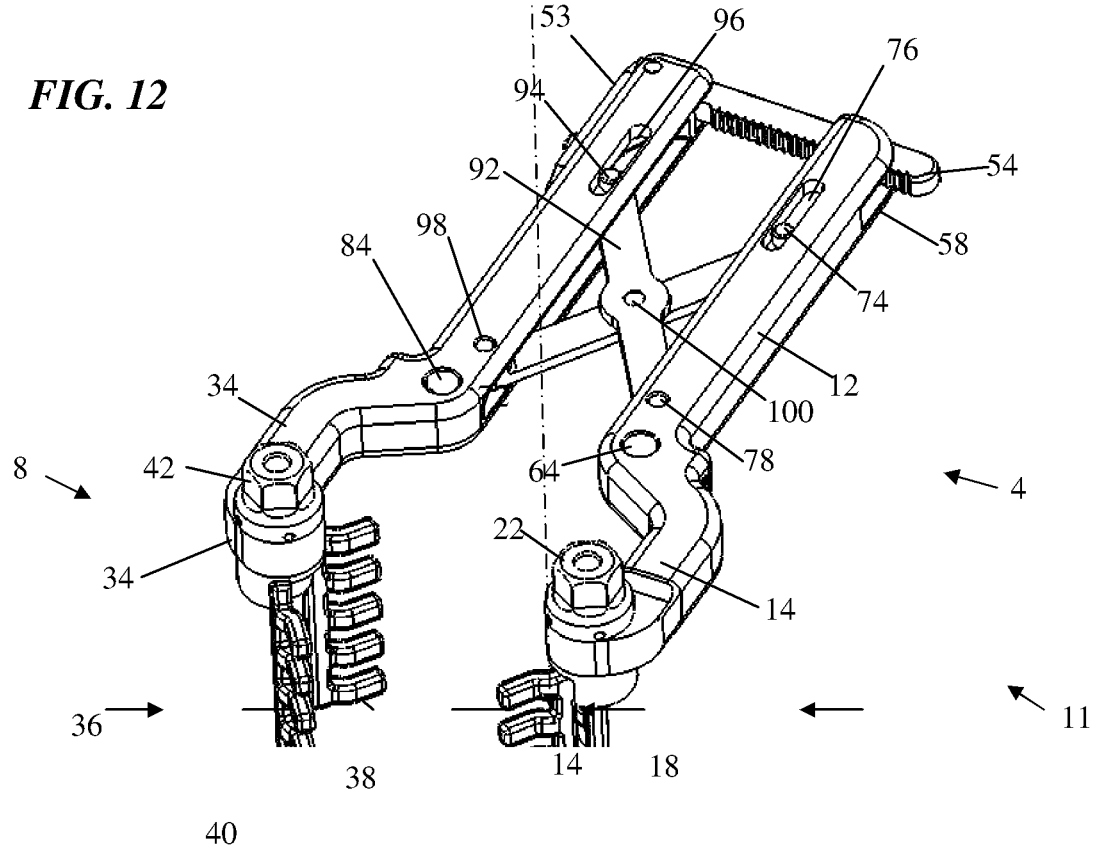
FIG. 12 provides a perspective view of an arm assembly.

FIG. 5 depicts the arms 12 and 32 of the arm assembly 4 in an open position. In this position it can be seen that arms 12 and 32 are joined one to another by a pair of cross members 72 and 92, which are joined together by a cross member pivot 100. The cross member 72 is connected to arm 32 via a pivot 98 and to arm 12 via a rod 74, which is moveable along the length of slot 76. Likewise the cross member 92 is connected to arm 12 via a pivot 78, and to arm 32 via a rod 94, which is moveable along the length of slot 96. One skilled in the art will recognize that the handle assembly 2 may be removed from the arm assembly 4 by removing the pins 62 and 82 from their respective holes 64 and 84, resulting in the device 11 depicted in FIG. 12. This may occur at any time, e.g. prior to or during sterilization of the retractor 10 or during a surgical procedure once the retractor 10 has been opened. Removal of the handle assem- bly 2 during surgery may afford a member of the surgical team greater freedom of motion, an improved field of view or both.

As can be seen in FIGS. 4 and 5, the blade assemblies 16 and 36 can be removed from the arm assembly 4. One may find it convenient to remove the blade assemblies 16 and 36 in order to expedite sterilization of the blade assemblies 16 and 36 and/or in order to exchange one or both blade assemblies 16 and 36 for other blade assemblies (e.g. different size blades, different configuration of blades, etc.) as discussed in more detail herein.

Figure 6:
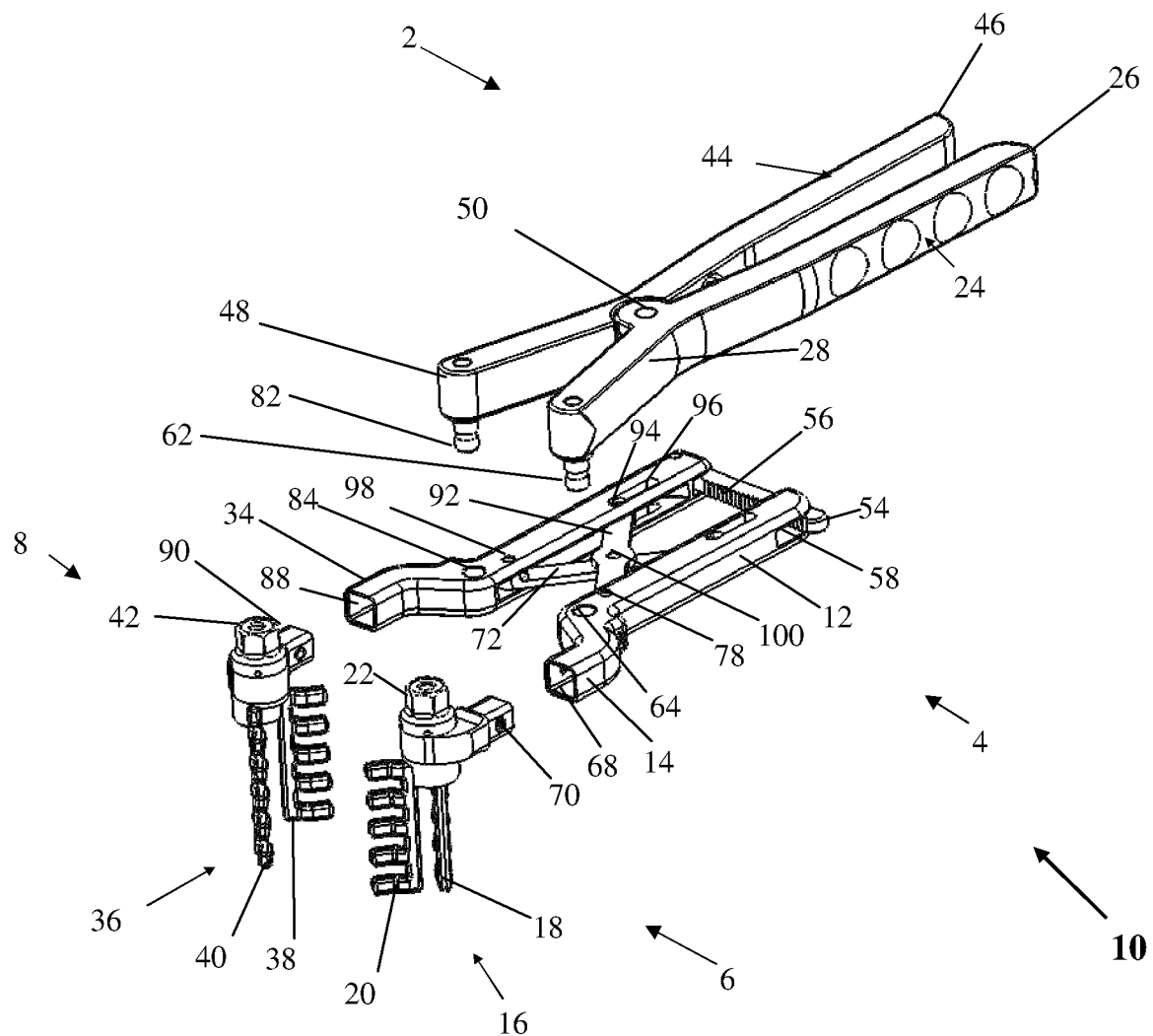
Figure 9:
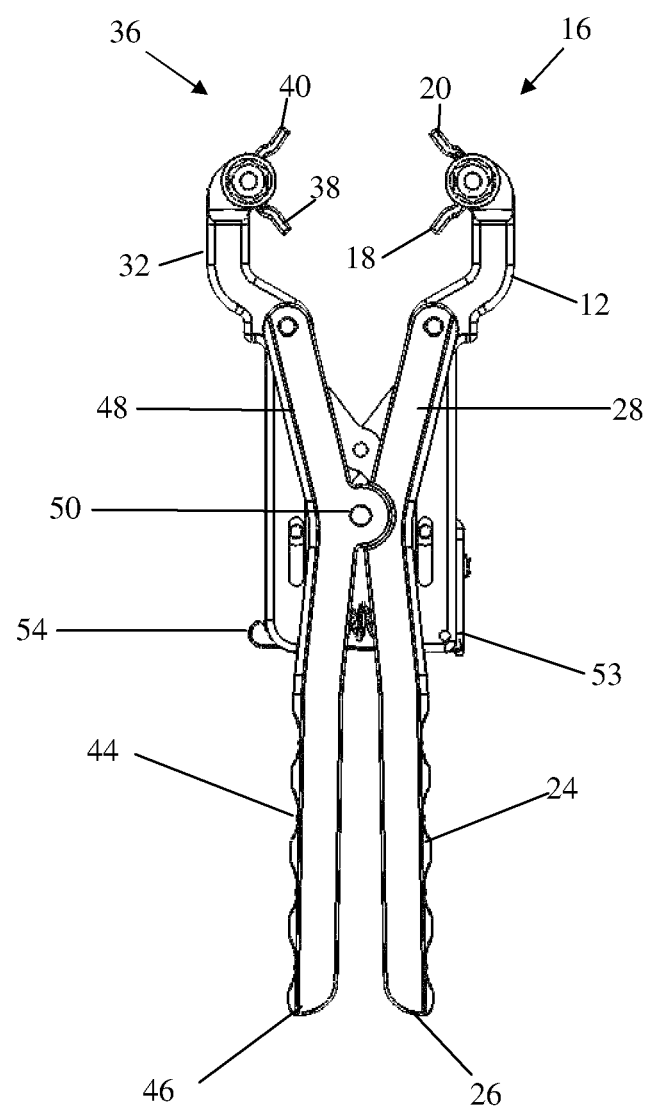
Figure 10:
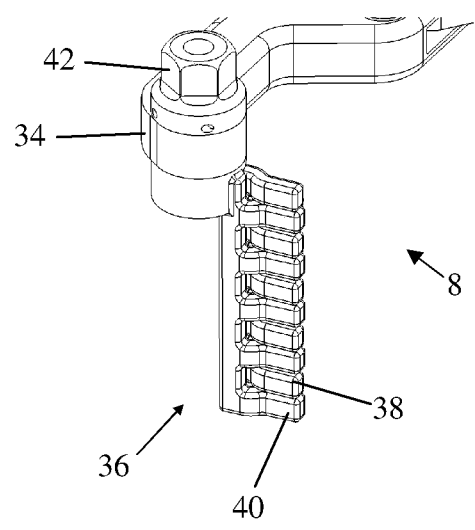
FIGS. 10 and 11 provide close-up views of a blade.
Figure 11:
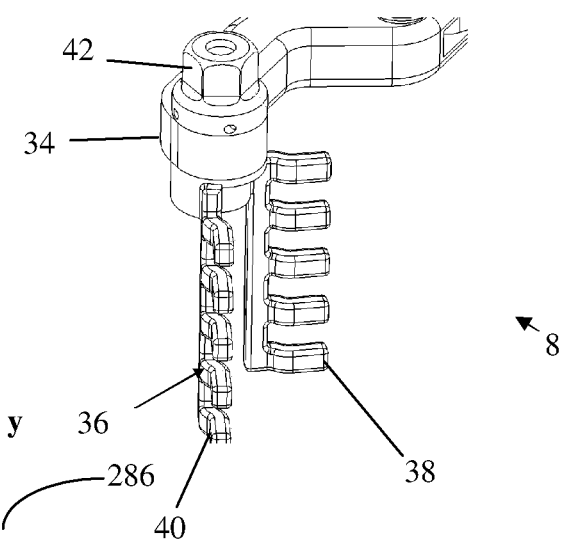

FIG. 6 is an exploded view of the retractor 10 with the blade assemblies 16 and 36 in an open position. FIG. 7 is a view of retractor 10 from above in a closed position. In this view it can be clearly seen that the biasing spring 52 tends to bias the handles 12 and 32 apart. Also shown in this view are axes z and z'. In some embodiments, the blade assem- blies 16 and 36 are adapted to rotate about the axes z, z'. In some embodiments, these added degrees of freedom permit the blade assemblies 16, 36 to be rotated outward so that they are farther apart at the lower parts of the blades than at the top. This allows the retractor 10 to create an even larger aperture without having to open the retractor 10 any farther. FIG. 8 shows a top view of the retractor 10 in an open position. As shown in FIG. 8 the ratchet 54 locks into position to hold the retractor 10 in an open position. FIG. 9 shows the retractor 10 from above with the blade assemblies 16 and 36 in open positions. FIGS. 10 and 11 are expanded views of blade assembly 36 in closed (FIG. 10) and open (FIG. 11) positions.

Figure 30:
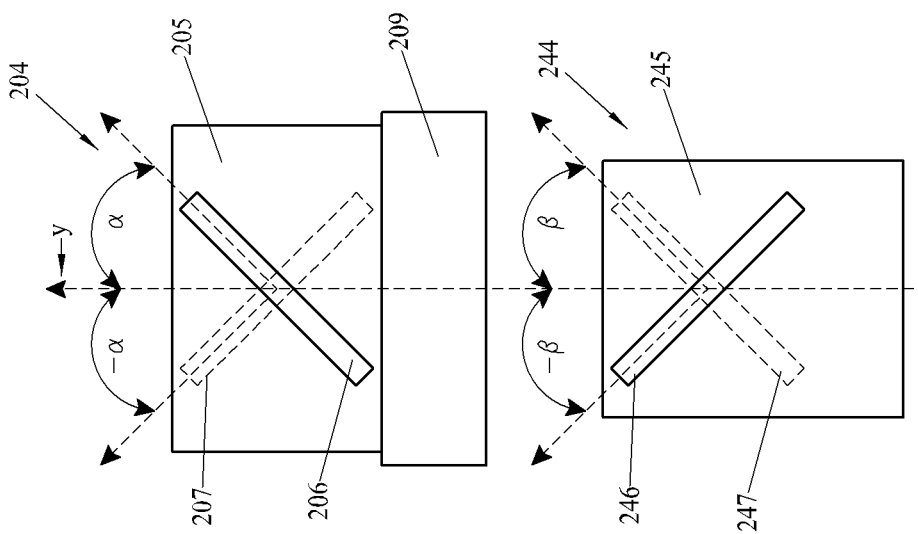
FIGS. 29-30 show side views of barrels of blade assemblies.
Figure 29:
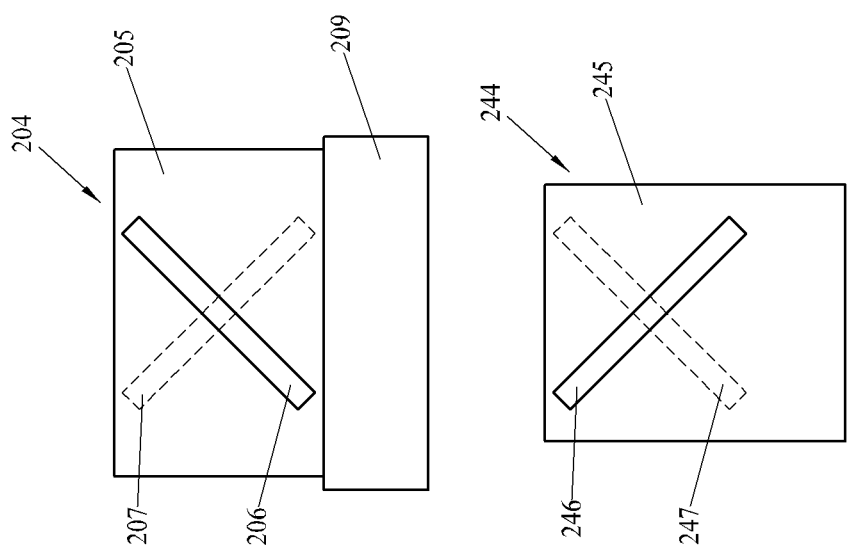

FIGS. 13-19 depict the assembly of an embodiment of a blade assembly 36, which comprises blades 40 and 38. Starting with FIG. 13, left opening blade subassembly 242 comprises blade 40, which is connected to inner barrel 244. The blade 40 comprises a plurality of teeth 254 connected to a bridge 252, which in turn is connected to the inner barrel 244 such that rotating the inner barrel 244 about axis y to the left (clockwise) results in the teeth 254 also turning to the left (clockwise). The inner barrel 244 has a slot 246 cut into the upper portion 245 of the inner barrel 244. Specifically, the upper portion 245 of the inner barrel 244 is that portion of the inner barrel 244 above the highest point at which the bridge 252 connects to the inner barrel 244. Not shown in this view is a corresponding slot on the other side of barrel 244, which is depicted in FIGS. 29 and 30 as slot 247, as discussed in more detail herein. The inner barrel 244 also has a lumen 248 through the inner barrel 244 and an engagement groove 250 circumscribing the inner barrel 244 above the slot 246.

Figure 31:
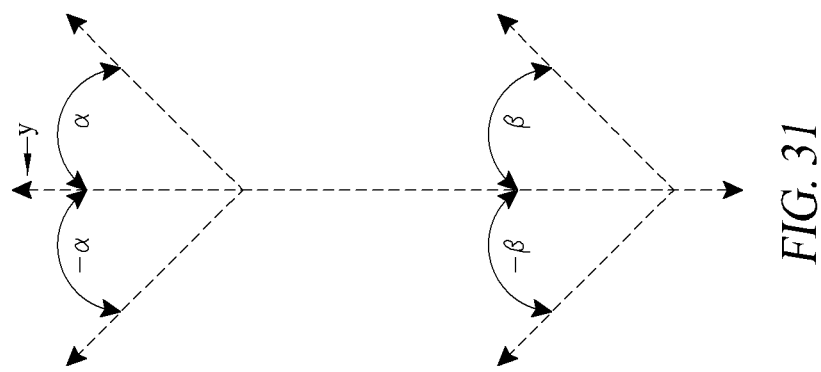

The right opening blade subassembly 202 comprises blade 38 comprising teeth 214 connected to a bridge 212, which in turn is attached to the outer barrel 204. The outer barrel 204 also possesses a lip 209, which is a ledge about the lower portion of the barrel 204. The bridge 212 is connected to the lip 209 such that rotation of the outer barrel 204 to the right (counterclockwise) about axis y results in the blade 38 also turning to the right (counterclockwise) about the axis y. The outer barrel 204 has a lumen 208 as well as a pair of slots 206, 207 cut into upper portion 205 of the barrel 204. For the sake of clarity, the upper portion 205 of the outer barrel 204 is that portion of the outer barrel 204 above the lip 209. The relationship of the slots 206, 207, 246 and 247 are depicted in FIGS. 29-31.

In FIG. 29 there is depicted a side view of barrel outer barrel 204 and inner barrel 244. For purposes of clarity, the barrels 244 and 204 are depicted without the additional components of the blade sub-assemblies attached, such as the blades. As can be seen in FIG. 29, slot 206 penetrates the upper portion 205 of outer barrel 204. Slot 207, shown in dotted lines, also penetrates the upper portion 205 of the outer barrel 204, albeit on the opposite side of the outer barrel 204. The outer barrel 204 also has a lip 209, as mentioned above, which is below the upper portion 205 of the outer barrel 204. Slot 246 penetrates the upper portion 245 of inner barrel 244. Slot 247, shown in dotted lines, also penetrates the upper portion 245 of the inner barrel 244, albeit on the opposite side of the inner barrel 244. As shown in FIG. 30, the inner barrel 244 and the outer barrel 204 have a common axis y, which passes vertically through the lumens (not shown) of the barrels 244 and 204. Axis y thus forms a C2 symmetry axis for slots 206 and 207, as well as for slots 246 and 247. More specifically, slot 206 forms an angle .alpha. with respect to the y axis, whereas the slot 207 forms an angle -.alpha. with respect to the axis y. Viewed from the vantage offered in FIG. 29, these angles .alpha. and -.alpha. have equal magnitude but opposite slope with respect to the axis y. In a like manner, the slot 246 forms an angle .beta., with respect to the axis y and the slot 247 forms an angle -.beta. with respect to the axis y. Thus slots 206 and 207 possess C2 symmetry about the axis y, as rotation of inner barrel 244 about the axis y results in slots 246 and 247 equivalently changing places, as these slots possess congruent angles with respect to the y axis and are located 180.degree. about the axis y from one another. Similarly, the slots 246 and 247 possess C2 symmetry about the axis y, as rotation of the slots 246 and 247 about the y results in slots 206 and 207 changing places, as these slots are essentially identical with respect to the y axis. Note that .alpha. and -.beta. have similar orientation as do -.alpha. and .beta. This accounts for the opposite rotation of the barrels 204, 244. Note also that in this embodiment angles .alpha., .beta., -.alpha. and -.beta. are essentially congruent, although in some embodiments of the application it may be desirable for .alpha. and -.alpha. to differ in magnitude from .beta. and -.beta. One of skill in the art would recognize that this latter arrangement would cause barrels 204 and 244 to rotate at different rates in opposite directions. Additionally, in the depicted embodiment it is presumed that the slots 206 and 207 are of equal length and start and end at essentially the same height as each other. However, it will be understood that the length of the slots 206 and 207 may be affected inter alia by the method used to form such features in the barrel 204 (e.g. machining, molding, etc.) and the assignment of C2 symmetry to the slot pair 206, 207 is intended as an illustrative convenience. More specifically, it is intended that breaking the strict mathematical C2 symmetry of the slots 206, 207 will not affect the operation of the application. Likewise breaking the strict mathematical C2 symmetry of the slots 246, 247 will not affect operation of the device. Thus, lengthening or shortening one of slots 206 or 207, moving one of the slots 206 or 207 up or down the barrel (along the axis y) or both changing the length and the position of one of the slots 206, 207 will not defeat the purpose of the device. Similarly, lengthening or shortening one of slots 246 or 247, moving one of the slots 246 or 247 up or down the barrel (along the axis y) or both changing the length and the position of one of the slots 246, 247 will not defeat the purpose of the device. Thus, for the slot pair 206, 207 to satisfy the C2 symmetry requirement for the purposes of the present device, it is sufficient that a portion of the slots 206, 207 satisfy the C2 symmetry requirement. Likewise, it is sufficient for a portion of the slot pair 246, 247 to satisfy the C2 symmetry requirement in order for the slot pair 246, 247 to satisfy the C2 symmetry requirement for the purposes of the present device. However, in the currently preferred embodiment, the slot pair 206, 207 possess strict C2 symmetry, as does the slot pair 246, 247, within reasonable tolerances (e.g. about +/−2%). It is also noted that, while the slots 206, 207, 246 and 247 are depicted as having constant slope with respect to the axis y, it is possible and well within the skill in the art for the slots to have serpentine or other curved slopes with respect to the axis y so long as the C2 symmetry requirement is satisfied through at least a portion of the slot pairs 206, 207 and 246, 247. (FIG. 31 shows the angles .alpha., -.alpha., .beta. and -.beta. independent of the barrels in order to provide easier visualization of their relationships to one another.)

Figure 13:
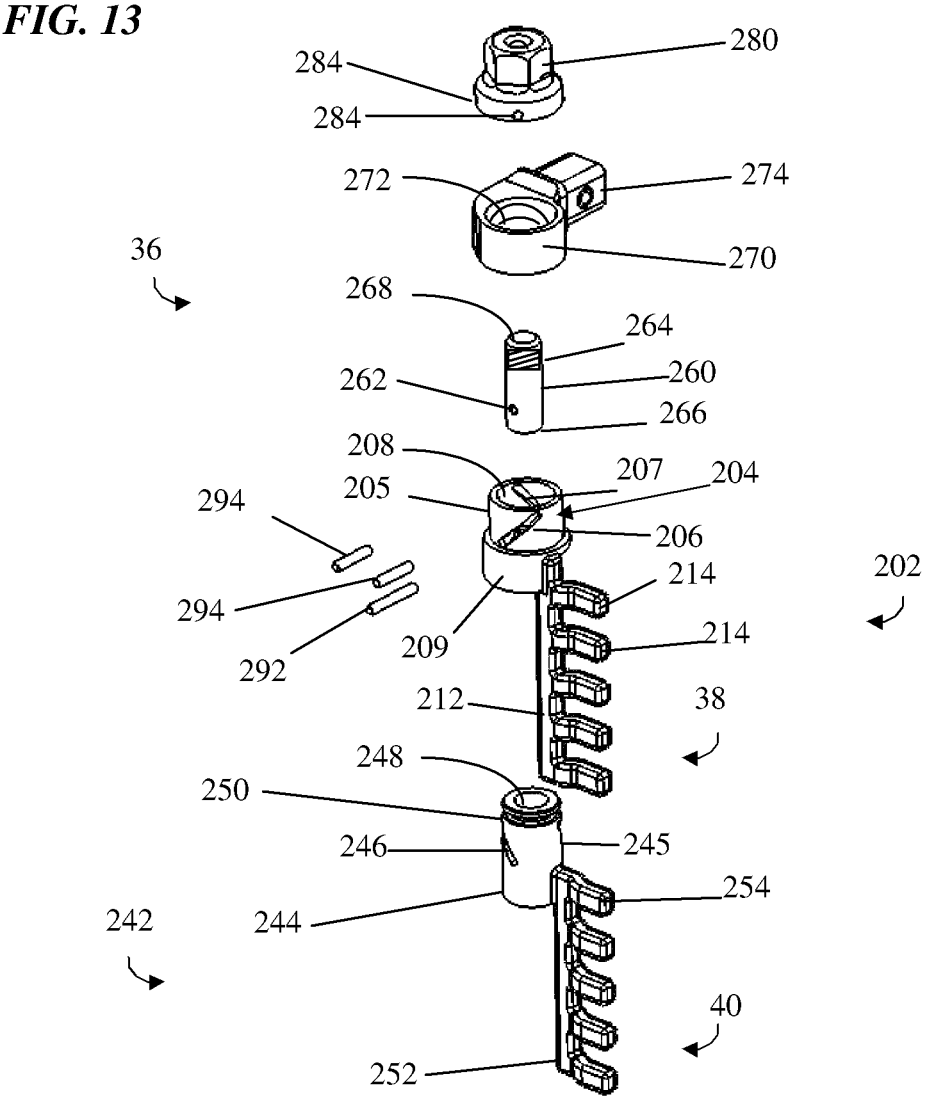
FIGS. 13-19 provide exploded views of a blade assembly, from which the assembly and operation of the blade assembly can be discerned.

FIG. 13 further depicts threaded plunger 260 having a bottom 266 and a top 268. The plunger 260 has a set of screw threads 265 near the top 268 and a hole 262 at a right angle to and passing through the y axis. Also depicted is a holder 270 comprising a lumen 272 and a projection 274. Additionally there is depicted an adjustment nut (or adjuster) 280 having internal threads 286 and two engagement holes 284. Also depicted are a connector pin 292 and two engagement pins 294.

Figure 14:
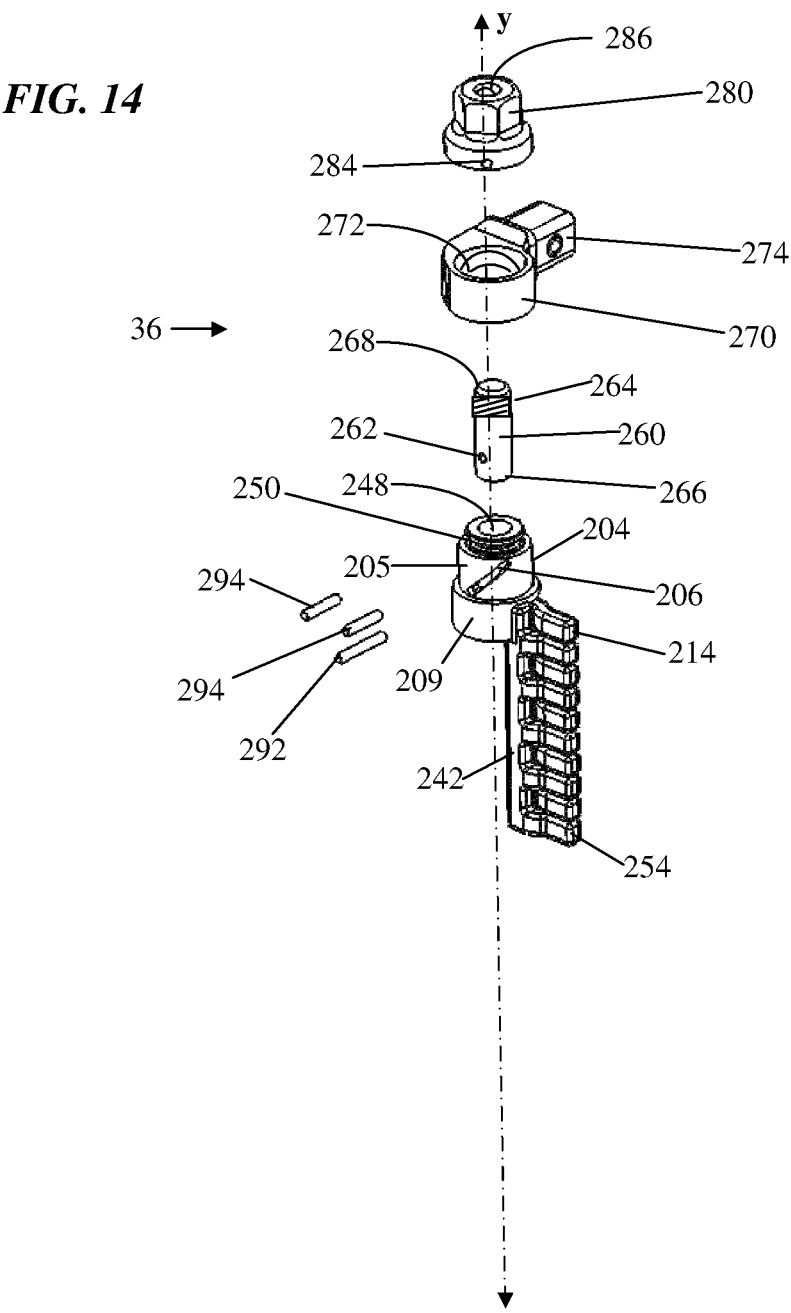
Figure 15:
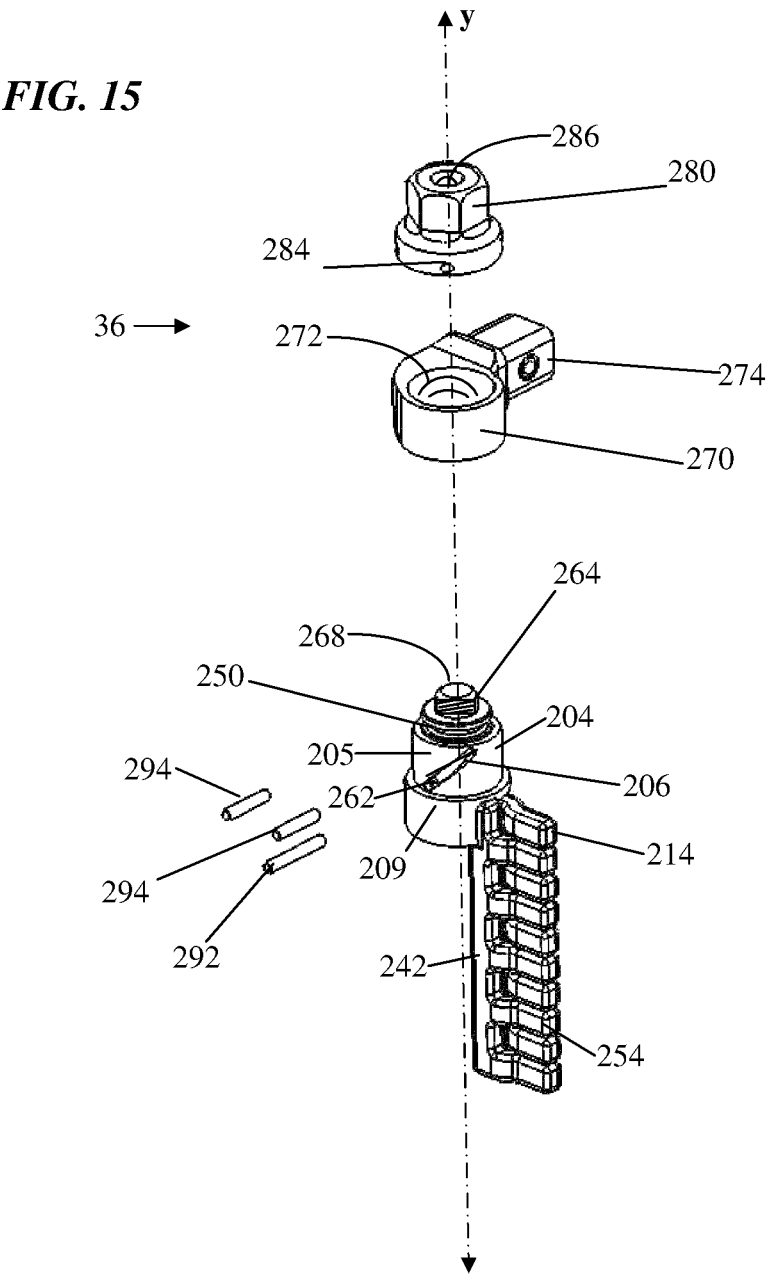
Figure 16:
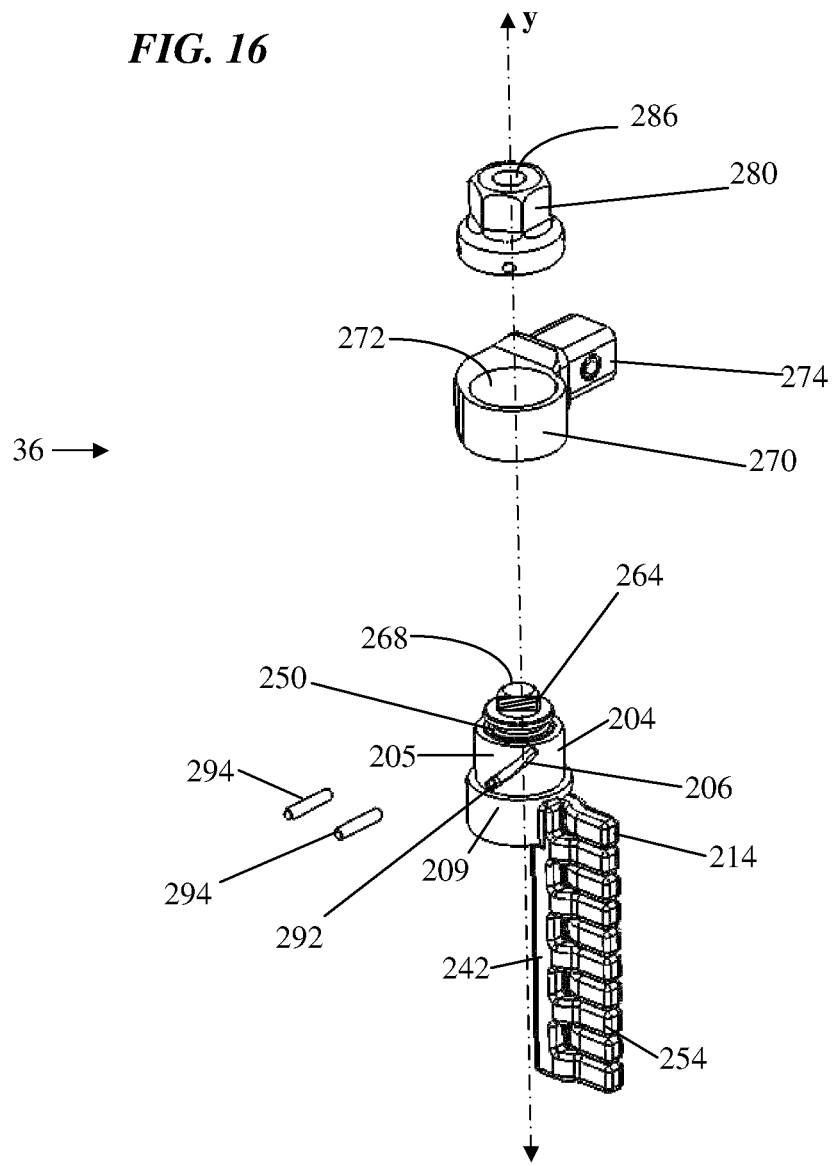
Figure 17:
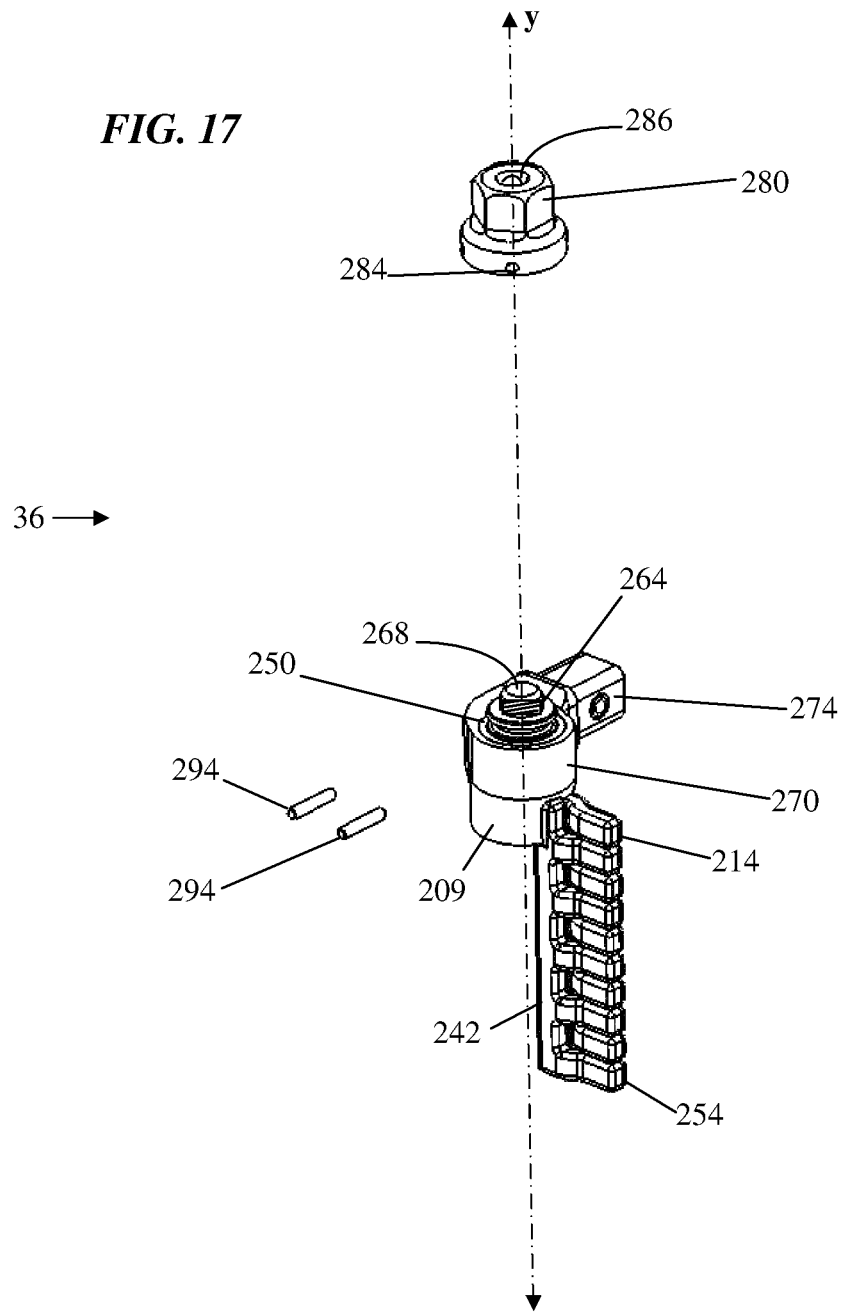
Figure 18:
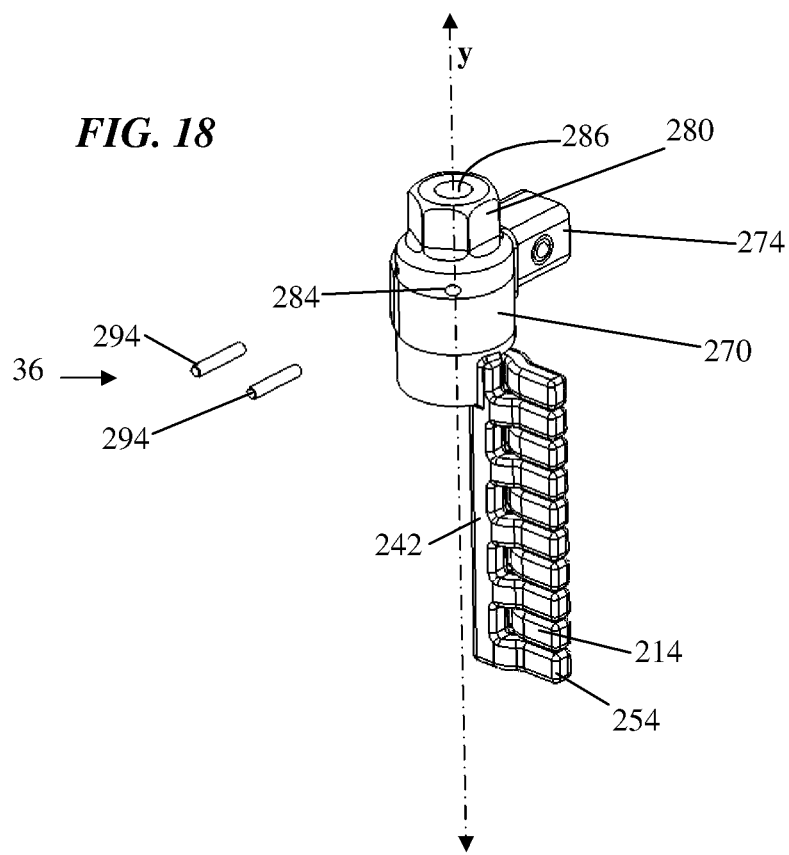
Figure 19:
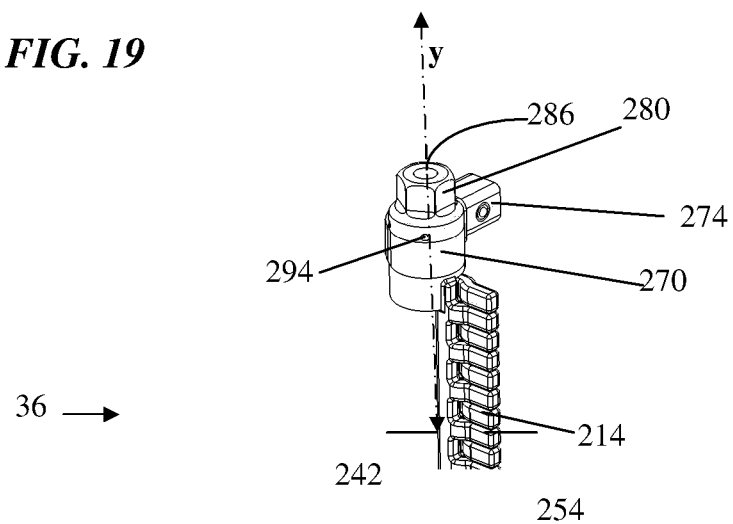
Figure 27:
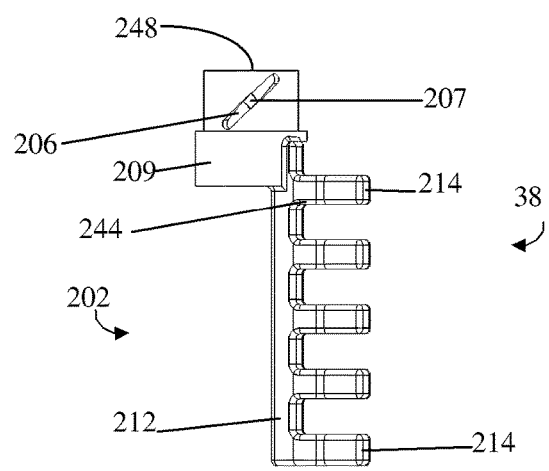
FIGS. 26-28 show side views of a second blade of a blade assembly.
Figure 28:
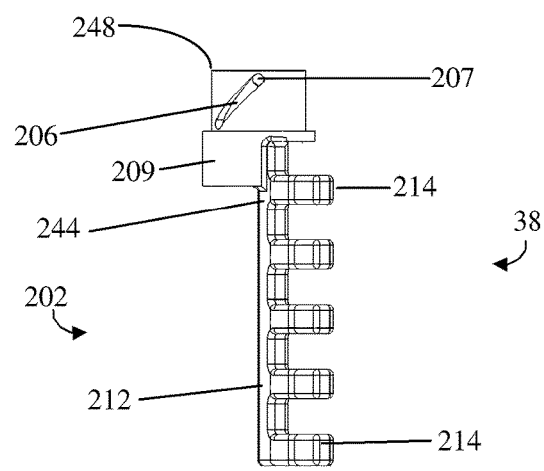

As seen in FIG. 14, the left turning barrel 244 fits within the lumen 208 of the right turning barrel 204. The plunger 260 then fits within the lumen 248 of the left turning barrel 244, as depicted in FIG. 15. In this configuration, the left turning slot 246 crosses the right turning slot 206 forming a passage 261 through which, as depicted in FIG. 16, the connector pin 292 fits. As depicted in FIG. 16, the blades 38 and 40 are in a closed position with the connector pin 292 at the bottom of the slots 24. In this configuration, it is seen that the two blades 38, 40 interlace to form a substantially planar blade pair, thus rendering the blade pair especially suitable for insertion within a small incision. One skilled in the art will recognize that moving the blades 38 and 40 apart will cause the barrels 244 and 204 to rotate in opposite directions, thereby causing connector pin 292 to rise along slots 246 and 206, thereby causing the plunger 260 to rise along the y axis. Conversely, pulling the plunger 260 up along the y axis would cause the connector pin 292 to rise along the slots 246 and 206, thereby causing the barrels 244 and 204 to rotate in opposite directions, thus causing the blades 40 and 38 to move apart. Conversely, starting with the connector pin 292 at the top of slots 246 and 206, pressing the plunger 260 down will cause the connector pin 292 to move down the slots 246 and 206, thereby causing the barrels 244 and 204 to rotate in opposite directions, thereby causing the blades 38 and 40 to rotate toward one another. As can be seen in FIG. 17, the assembly of barrel 244, barrel 204 and plunger 260 fits through the lumen 272 of the holder 270 so that the threads 264 toward the end 268 of the plunger 260 are visible above the lumen 272 of the holder 270 and the lip 209 of the outer barrel 204 abuts the holder 270. As can be seen in FIG. 18, the adjustment nut (adjuster) 280 fits over the end 268 of the plunger 260 and is held in place by pushing the engagement pins 294 through the engagement holes 284. One of skill in the art will appreciate that the engagement pins 294 thus engage the engagement groove 250 on the barrel 244, thereby permitting the adjustment nut 280 to freely turn about the y axis, but preventing the adjustment nut 280 from moving up or down along the y axis. The inner threads 286 of the adjustment nut 280 thus engage the outer threads 264 of the plunger 260. Turning the adjustment nut 280 about the y axis in one direction causes the plunger 260 to move upward along the y axis, while turning the adjustment nut 280 in the opposite direction causes the plunger 260 to move downward along the y axis. As explained above, movement of the plunger 260 causes movement of the connector pin 292 up and down the y axis. Movement of the pin 260 in one direction creates force in one direction on the slots in one barrel and in the opposite direction on the slots in the other barrel. Thus, the adjustment nut 280 can be turned to open an close the blade assembly 36. FIG. 19 shows a fully assembled blade assembly 36 in the closed position.

Figure 20:
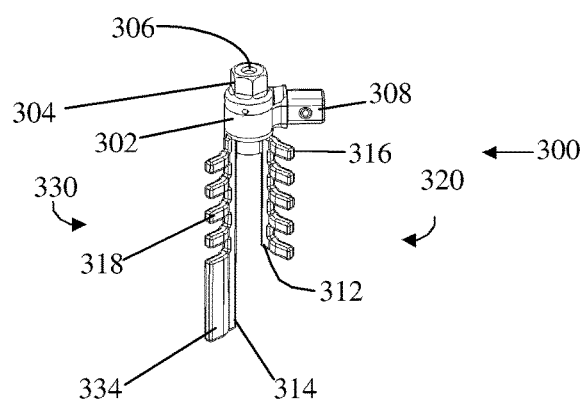
FIGS. 20-22 show various blades that may be employed in blade assemblies.
Figure 22:
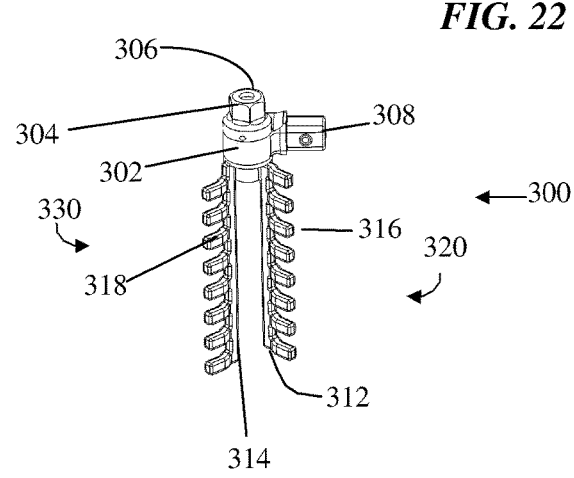

The blades used in the blade assemblies may have a variety of configurations. FIG. 20 shows an alternate embodiment of a blade assembly 300 according to the device, which comprises a holder 302 connected to a projection 308, which is adapted to reversibly insert into the end of an actuator arm (not shown). The blade assembly 300 further comprises an adjuster 304 and a plunger 306. The adjuster 304 is threaded on the inside, just as the plunger 306 is threaded on its outer surface, so that turning the adjuster causes the plunger 306 to move up and down. The plunger 306 operates through the holder 302 to turn the blades 320, 330 in opposite directions as described in more detail with regard to FIGS. 1-13 above. In particular, the plunger 306 operates to turn inner barrel 322 in the opposite direction to outer barrel 332 essentially as described above. Inner barrel 322 is connected to bridge 312 from which project teeth 316. Together bridge 312 and teeth 316 form the blade 320. Outer barrel 332 is connected to bridge 314 from which project teeth 318 and fan 334. Together bridge 314, teeth 318 and fan 334 form the blade 330.

Figure 21:
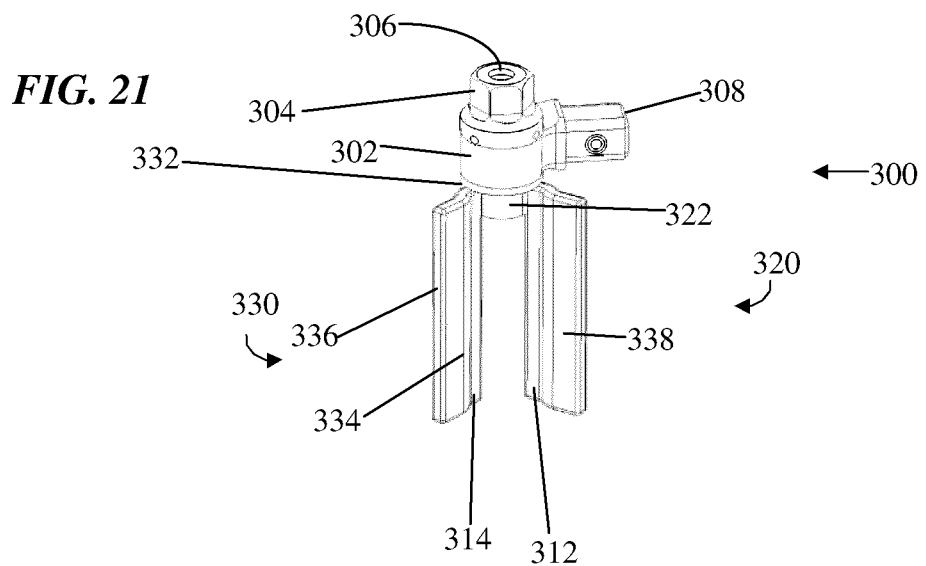
Figure 23:
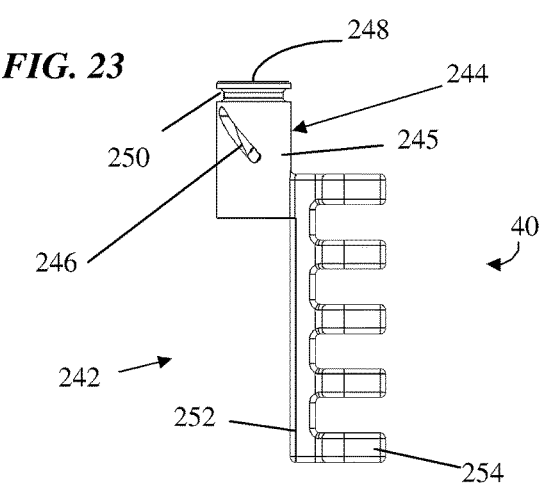
FIGS. 23-25 show side views of a first blade of a blade assembly.
Figure 24:
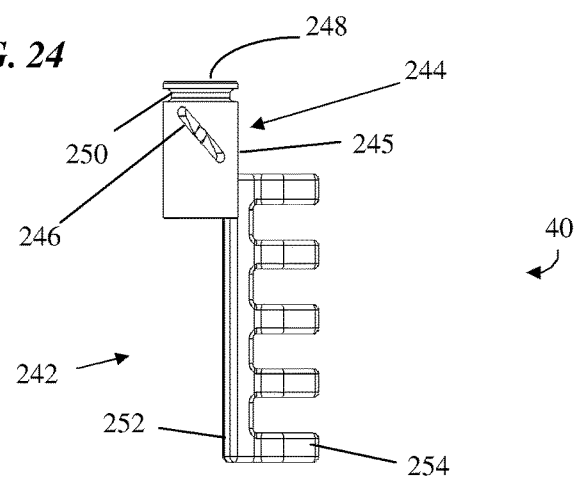
Figure 25:
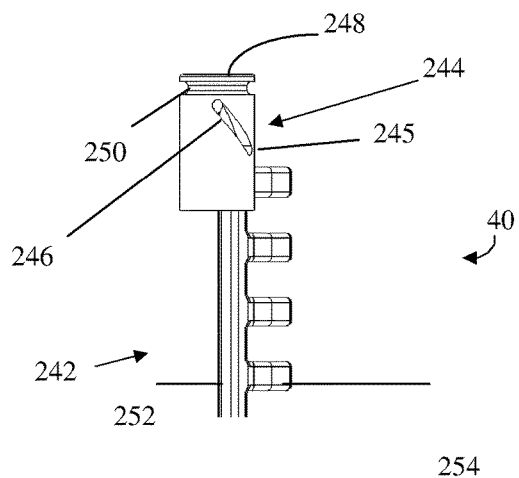
Figure 26:
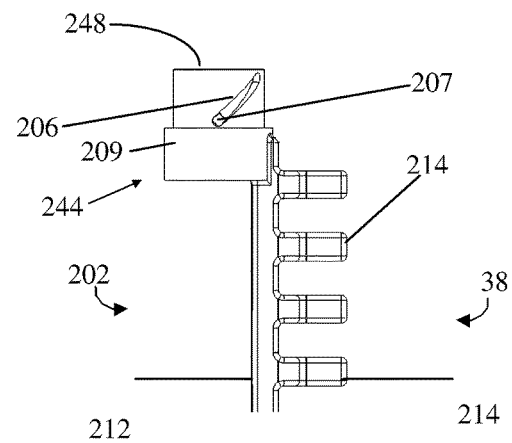

Another embodiment of a blade assembly 300 is shown in FIG. 21, where the blade 320 comprises fan 338; and blade 330 comprises fan 336. As can be seen in FIGS. 22-28, blades 320, 330 can have a variety of lengths of bridges 312, 314, teeth 316, 318, etc. (In these figures, the same numbering is used as in FIGS. 1-13.

In some embodiments, contemplates kits comprising a retractor. In some embodiments, the kit comprises a single actuator (e.g. a removable handle and arm assembly as described herein and depicted in the figures, a scissor-like assembly, etc.) and a plurality of removable and exchangeable blade assemblies. In some embodiments, the kit comprises at least three blade assemblies having amongst the three blade assemblies at least two distinct blade configurations. In other embodiments, the kit comprises from 3 to 12 blade assemblies having amongst the several blade assemblies from 2 to 12 distinct blade configurations. In some embodiments, the kit comprises at least two pairs of identical or substantially similar blade assemblies. In other embodiments, the kit comprises from 2 to 10, especially about 2 to 5 such pairs of blade assemblies. The blade configurations that are represented in such kits can include comb-like blades, interlocking comb-like blades (as depicted e.g. in FIGS. 1-12), fan-like blades (as depicted in FIG. 21), combinations of toothed and fan-like blades (as depicted in FIG. 20), etc.

It is noted that in some embodiments the threads 286 and 268 can be canted with respect to the y axis to provide mechanical advantage to the operator opening and closing the blade assembly 36. In particular, the threads may be canted so that one full rotation of the nut 280 will result in the connector pin 292 rising from 1/10 to all the way from its lowest position to its highest position. In some embodiments, the user will be required to perform from about 1 to about 10 full rotations, especially about 2 to about 8 full rotations, and in particular about 2, 3, 4, 5, 6, 7 or 8 full rotations of the nut 280 to cause the connector pin to traverse the length of the slots 206 and 246, thereby moving the blade assembly 36 from its fully open to its fully closed position or vice versa.

Figure 33:
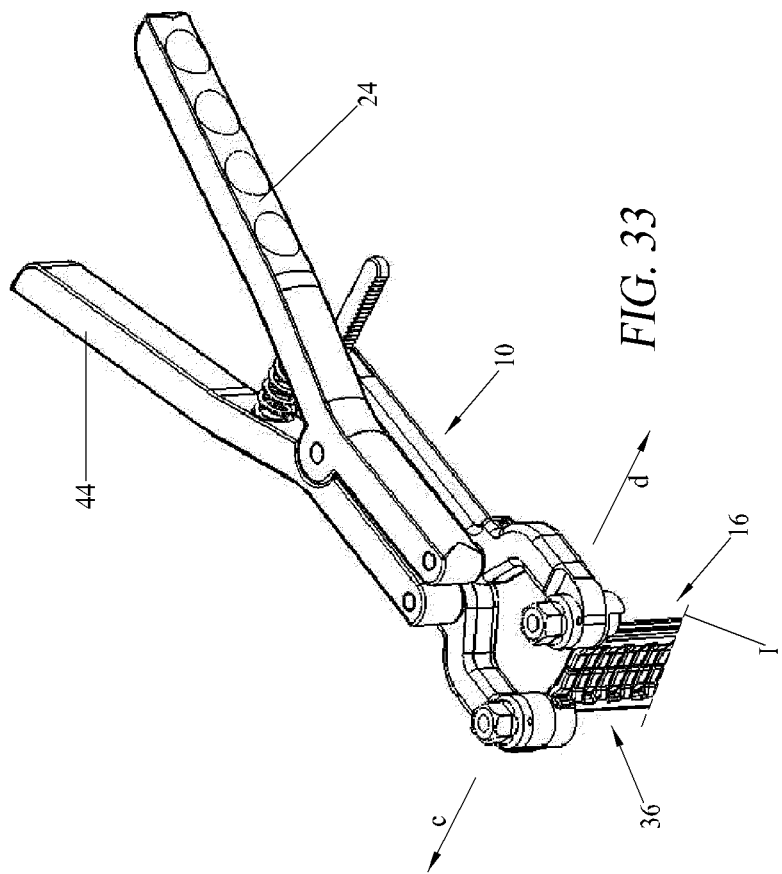
FIGS. 32-35 show perspective views of a retractor of the invention in operation. A surgeon makes an incision having length L, into which the closed blade assemblies of the retractor are inserted. The surgeon then opens the retractor to create a lengthwise opening having length L', wherein L'>L. Finally the surgeon opens the blade assemblies to create a L'×W' aperture. In some embodiments, the handles 24, 44 can be removed from the arm assembly to permit the surgeon even greater ability to see and operate on the tissue to be treated.
Figure 32:
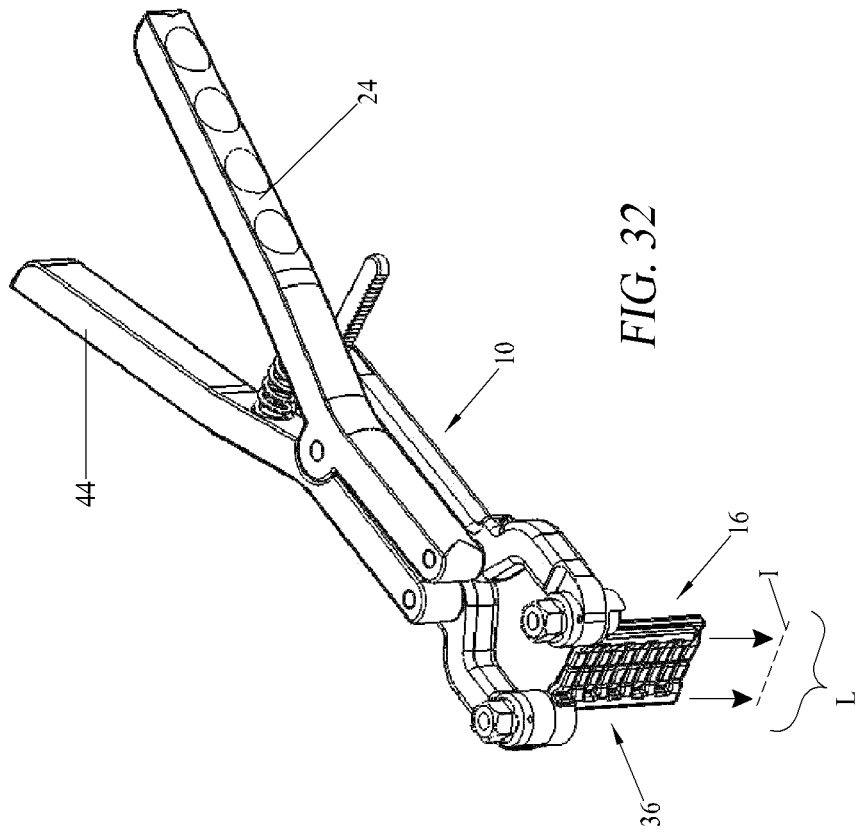
Figure 35:
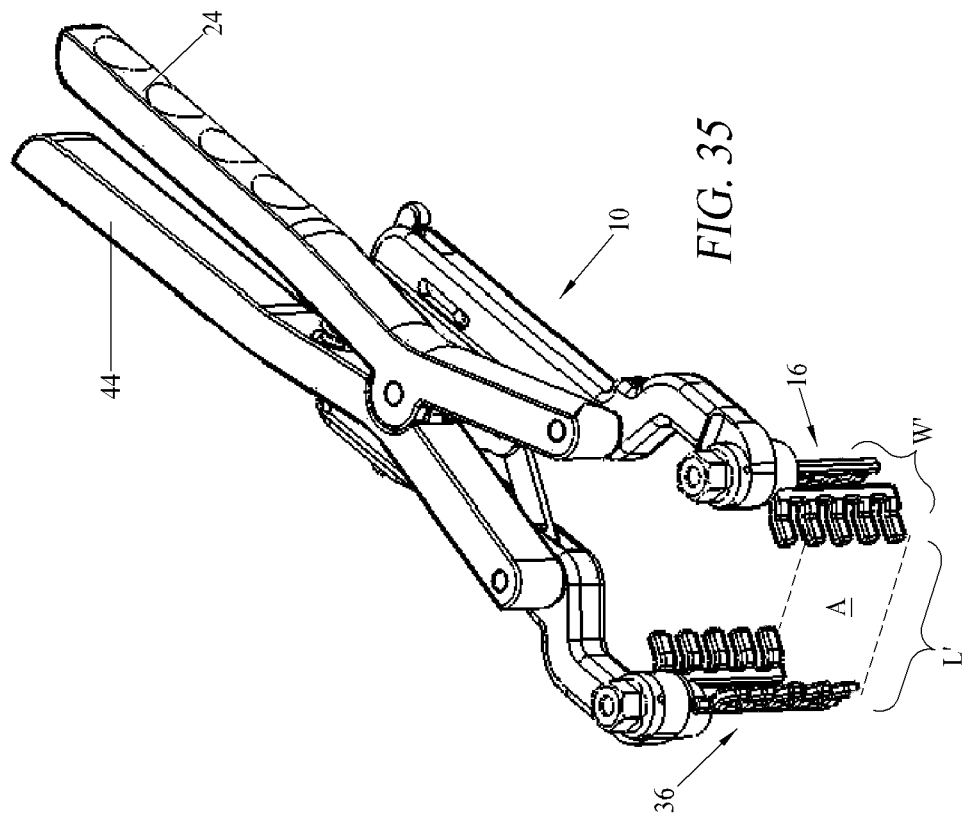
Figure 34:
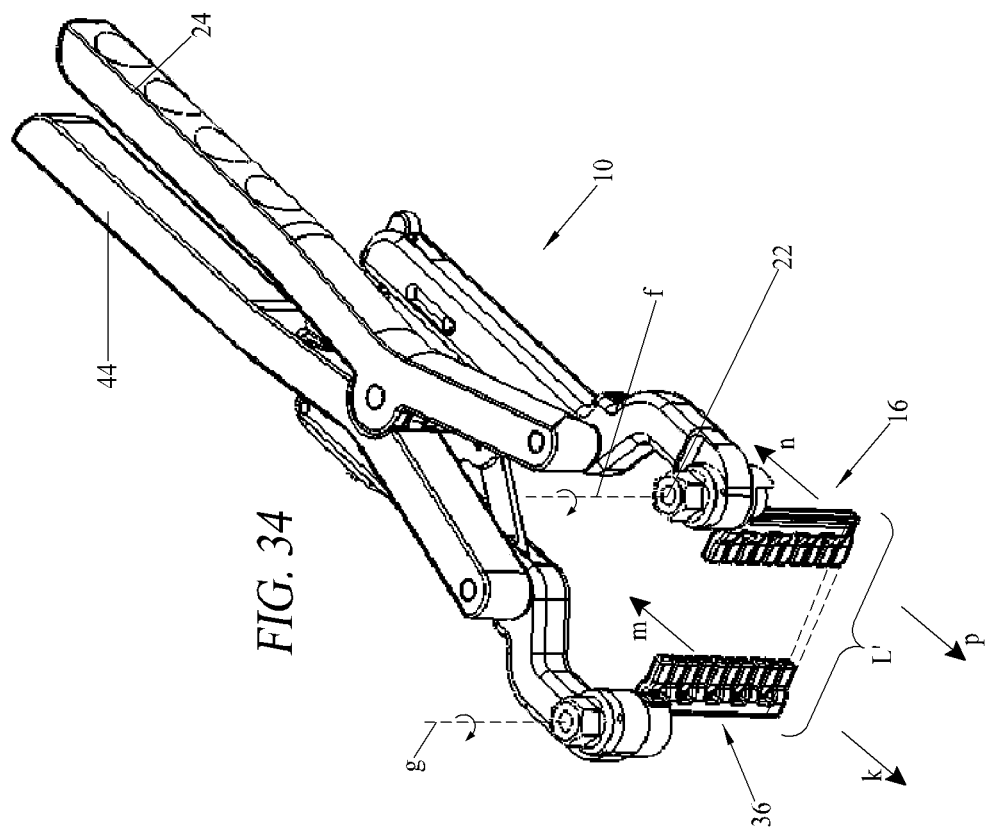

A method according to the an embodiment can be visualized by referring to FIGS. 32-35. In FIG. 32, there is depicted a retractor 10 comprising a pair of handles 24, 44 and a pair of blade assemblies 16, 36 as described in more detail herein. An incision I having a length L is made in a suitable tissue, such as the skin overlying or in proximity to the lumbar region of the spine. The blade assemblies 16, 36 are in a closed position and aligned relatively parallel to one another. In FIG. 33, the blade assemblies 16, 36 have been inserted into the incision I. Pressure on handles 24, 44 causes the retractor 10 to open: i.e. blade assemblies 16, 36 move apart from one another in the general directions of directional arrows c, d, respectively. As can be seen in FIG. 34, the incision I is stretched open in the direction of the directional arrows c and d so that it obtains a length L' greater than length L of the incision. Turning the adjusters 22, 24 in the direction of the curved arrows about the axes f and g, respectively results in the opening of the blade assemblies 16, 36, causing the incision I to open as can be seen in FIG. 35. As can be seen in FIG. 35, the aperture A is opened having a length L' and a width W'. The aperture A thus provides an access area of dimensions L'.times.W' for surgical personnel to view the operating field, to pass instruments, sutures, implants and other surgical materials through the aperture. Reversal of the steps outlined in FIGS. 32-35 results in a final incision I having substantially the same length L and essentially no width, just as the original incision I. By way of comparison, in order for a prior art device having a pair of blades to crease such an aperture, the incision I would have to have a length L' and the blades would have to have a width of L'. Thus, the present embodiment permits the use of a much smaller incision to create the aperture. Thus, the present embodiment permits less invasive surgical methods, quicker and more comfortable recovery from surgery and potentially cost savings for the medical coverage provider.

Figure 36A:
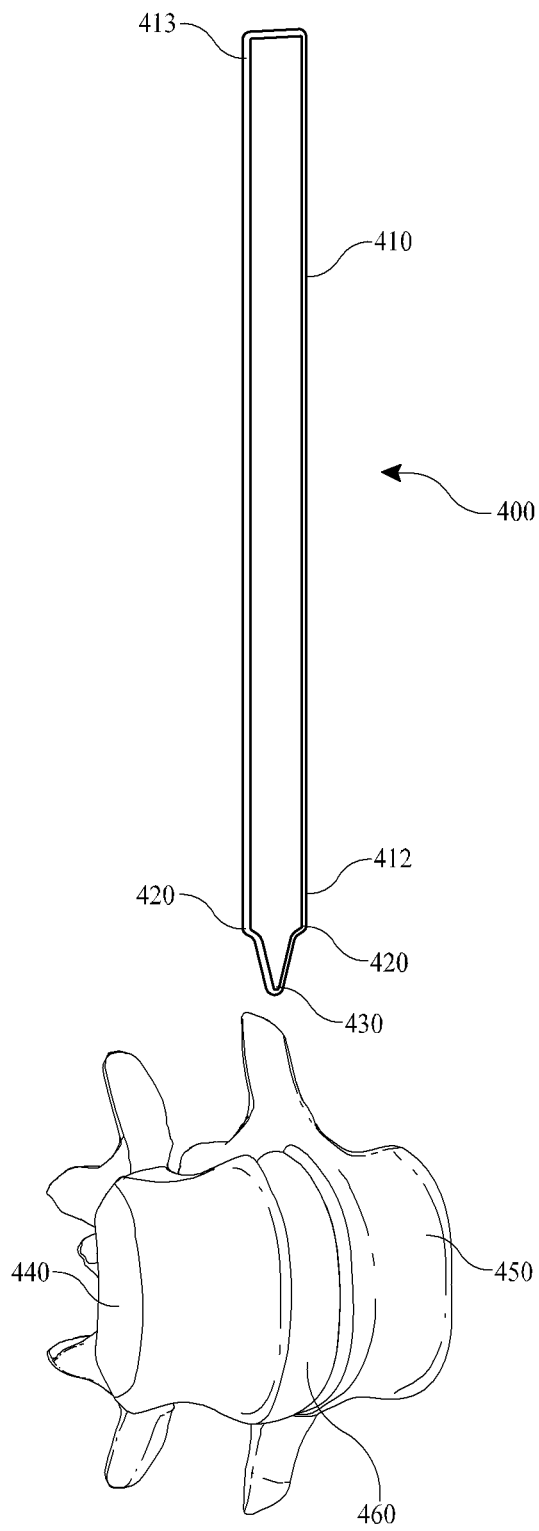
FIGS. 36A-36F show the use of a probe to insert a retractor system to form an operative channel through the tissue of a patient to access a portion of the patient's spine.

FIGS. 36A-36F illustrate a probe 400 and a method for its use in conjunction with the retractor 10. FIG. 36A illustrates a probe 400 and a portion of a spine, including a first vertebra 440, a second vertebra 450, and a disc 460 disposed between the first vertebra 440 and the second vertebra 450. The probe 400 can have a probe body 410, a proximal end 413, a distal end 412, an anchor tip 430, and a distal shoulder 420. The anchor tip 430 can be disposed at the distal end 412 of the probe body 410. The distal shoulders 420 can be located at the distal end 412 of the probe 400 at the base of the anchor tip 430. In modified embodiments, the probe 400 can have a distal end of a different shape. For example, the distal end 412 can be formed without the shoulder 420 and/or without the tip 430 and/or one of both elements can be modified in shape.

Figure 37A:
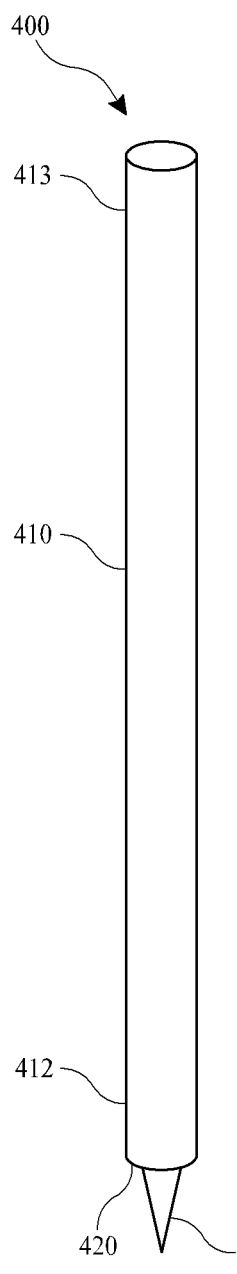
FIGS. 37A-37D show various embodiments of a probe system which can be used to insert a retractor system to form an operative channel through the tissue of a patient.
Figure 37B:
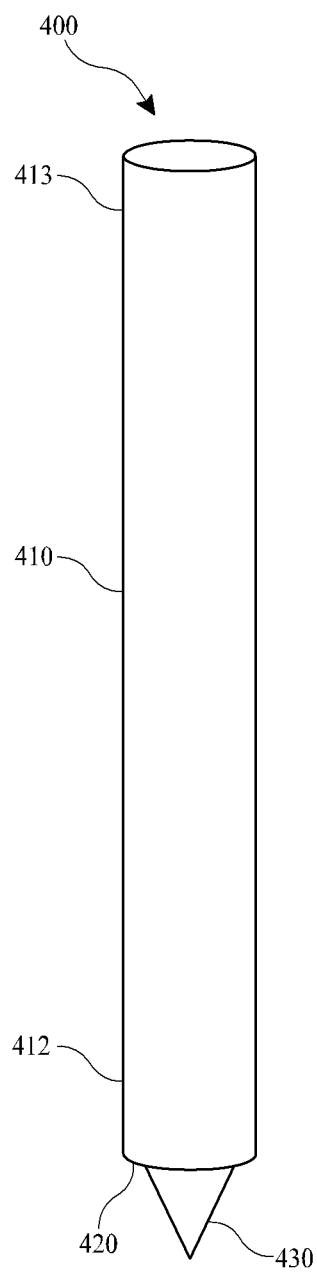

In some embodiments, the probe 400 can be rectangular in horizontal cross section (i.e., the plane bisecting the probe 400 perpendicular to the axis formed by the proximal end 413 and the distal end 412). In other embodiments, the probe 400 can be circular in horizontal cross section or oval cross section. FIG. 38A-38I illustrate some representative cross sectional shape the probe 400 can have, including: a circle (shown in FIG. 38A); an oval (shown in FIG. 38B); a triangle (shown in FIG. 39C); a flattened oval (shown in FIG. 38D); a thin flattened oval (shown in FIG. 38E); a rounded rectangle (shown in FIG. 38F); a thin rounded rectangle (shown in FIG. 38G); a rectangle (shown in FIG. 38H); and a thin rectangle (shown in FIG. 38I). In yet other embodiments, the probe 400 can be any other appropriate shape, including but not limited to square, triangular, and ellipsoid. A rectangular cross-sectional shape can include a shape in which the corners of the device are rounded and/or arrangements in which the adjacent sides are not exactly perpendicular (e.g., plus or minus 10 degrees, 5 degrees, 1 degrees or 0.1 degrees from perpendicular) and/or when the sides of the probe have ridges, bends that deviate 10%, 5%, 1% or 0.1% from the width or length of a side. FIGS. 37A and 37B illustrate a probe 400 with circular cross section and a probe 400 with an oval cross section respectively.

In some embodiments, the probe 400 can be constructed out of a biocompatible metal, such as but not limited to stainless steel, titanium, and cobalt chrome moly. In other embodiments, the probe 400 can be constructed out of a biocompatible ceramic. In still other embodiments, the probe 400 can be constructed out of any stiff, biocompatible material, including such classes of materials as metals, ceramics, and polymers, or any combinations thereof.

In some embodiments, the probe 400 can have a vertical length (i.e., length from the distal end 412 to the proximal end 413) in the range of about 5-50 cm, about 6-40 cm, about 7-30 cm, about 7-20 cm and about 8-10 cm or any other range which is appropriate to allow the probe 400 to function as desired. In some embodiments, the probe 400 can have a width in its largest, non-vertical dimension, in the range of about 5 mm-5 cm, about 6 mm-4 cm, about 7 mm-3 cm, and about 8 mm-2 cm, including about 1.5 cm.

In some embodiments, the distal shoulders 420 can extend horizontally in from the edges of the probe 400 in the range of about 0.1-5 mm, about 0.2-4 mm, about 0.3-3 mm, about 0.4-2 mm, about 0.5-1 mm, and about 0.6-0.8 mm. In some embodiments, the external corners where the distal shoulders 420 meet the vertical edges of the probe 400 can be squared. In other embodiments, the external corners where the distal shoulders 420 meet the vertical edges of the probe 400 can be rounded or smoothed. In some embodiments, the distal shoulders 420 can be machined flat on the bottom (particularly in such embodiments in which the probe 400 is a shape other than rectangular). In other embodiments, the distal shoulders 420 can be sharpened across their entire length to form a blade along their entire length. In other embodiments, the distal shoulders can be are sharpened across only a portion of their length to form a blade along only a portion of their length. For example, in some embodiments, only half of each distal shoulder 420 is sharpened (e.g., either the half of the distal shoulders 420 abutting the anchor tip 430 or the half of the distal shoulders 420 abutting the edges of the probe 400).

In some embodiments, the anchor tip 430 can extend downward from the distal end 412 of the probe 400. In some embodiments, the anchor tip 430 can be substantially triangular (illustrated in FIG. 36A). In other embodiments, the anchor tip 430 can be substantially parabolic. In other embodiments, the anchor tip 430 can be a small cylindrical member, such as a trocar. In yet other embodiments, the anchor tip 430 can be any shape which allows anchoring of the probe 400 in tissue. In some embodiments, the edges of the anchor tip 430 can be machined to be substantially smooth. In other embodiments, the edges of the anchor tip 430 can be sharpened to form a blade.

In some embodiments, at least a portion of the vertical edges of the probe 400 can be sharpened. In some of these embodiments, the portion of the edges of the probe 400 which are sharpened can be disposed near the distal end 412 of the probe 400. As a representative example, 1-5 cm of the edges of the probe 400 extending up from the distal end 412 and distal shoulders 420 can be sharpened to form a blade to facilitate insertion of the probe 400 into corporeal tissue of a patient.

In operation, the probe 400 can be inserted into a patient, preferably into an anchorable location, such as a collagenous tissue, bone, or vertebral disc. FIG. 36A illustrates the probe 400 being inserted into a patient (not fully shown) toward the spine (only a first vertebra 440, second vertebra 450, and disc 460 are illustrated in this representative example). The probe 400 illustrated in FIG. 36A is a thin, blade like rectangular probe 400 with a triangular anchor tip 430 and squared corners where the distal shoulders 420 meet the edges of the probe 400. The structure of the probe 400 can facilitate its passage through tissues of a patient which can run parallel to the flat surfaces of the probe. In operation, a physician can select a location in which he desires to use a retractor 10 to form an operative channel in the tissues of the patient (the spine will be used in this example for illustration purposes only). After the surgeon selects the location for retractor 10 placement, he can insert the probe 400 by placing the anchor tip 430 against the surface of the patient and applying pressure to the proximal end 413. The physician can then continue to apply pressure, thereby pushing the probe 400 through the tissue of the patient, until the probe 400 is fully in place. In some embodiments, an imaging modality can be used during the insertion of the probe 400. As a representative, non-limiting example, X-ray fluoroscopy can be used during insertion of the probe 400 to ensure correct placement. Any appropriate imaging modality can be used to monitor the placement of the probe 400. In some embodiments, a surgeon can make an incision with another instrument, such as a scalpel, prior to the insertion of the probe 400, into which the probe 400 is inserted.

Figure 36B:
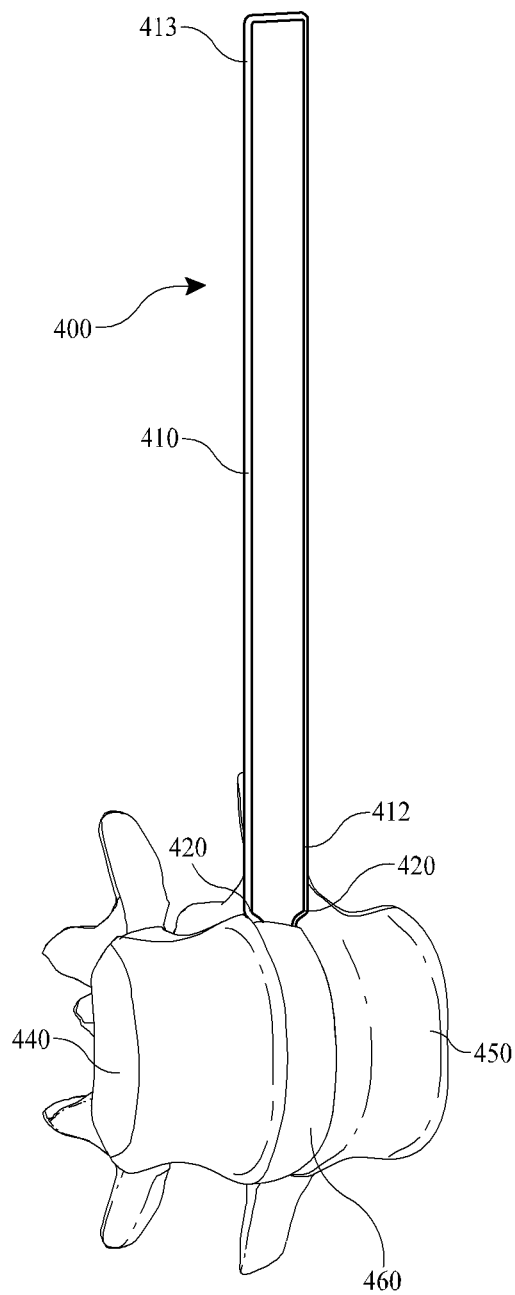

FIG. 36B illustrates the probe 400 fully in place in a patient. The probe 400 has been inserted into the side of the spinal column (here defined by a first vertebra 440, a second vertebra 450, and the disc 460 between them). FIG. 36B illustrates the placement of the probe 400 in a location in which the anchor tip 430 can anchor the probe 400. As shown in FIG. 36B, the probe 400 has been inserted into the patient until the anchor tip 430 has sunk at least some distance into the disc 460 between the first vertebra 440 and second vertebra 450. The anchor tip 430 has sunk into the disc 460 up until the distal shoulders 420 of the probe 400. The distal shoulders 420 serve in this example to limit the possible insertion depth of the anchor time 430 of the probe 400.

Figure 36C:
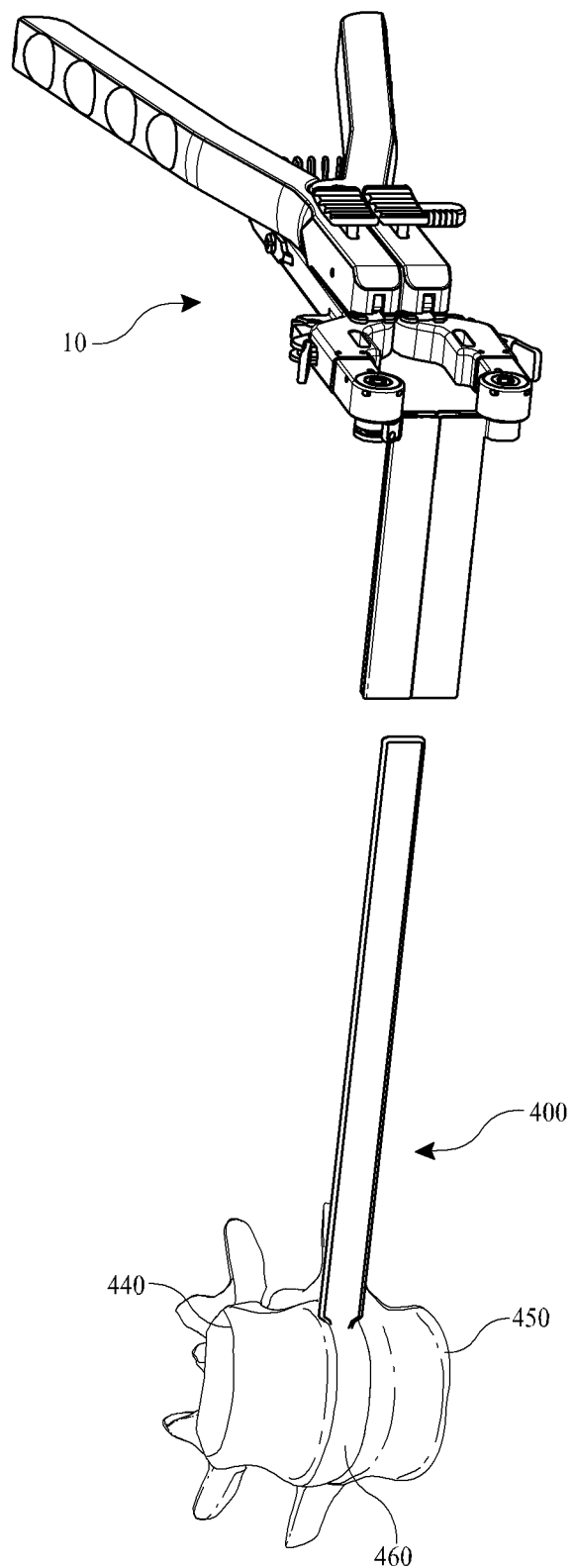

FIG. 36C illustrates a retractor 10 (as disclosed herein) and a placed probe 400. The retractor 10 has blades as disclosed above which, when in their close conformation, fit substantially closely around the probe 400. The blades of the retractor 10 can be any type of blade as described above, including but not limited to a comb style blade, a fan style blade, or a combination style blade.

Figure 36D:
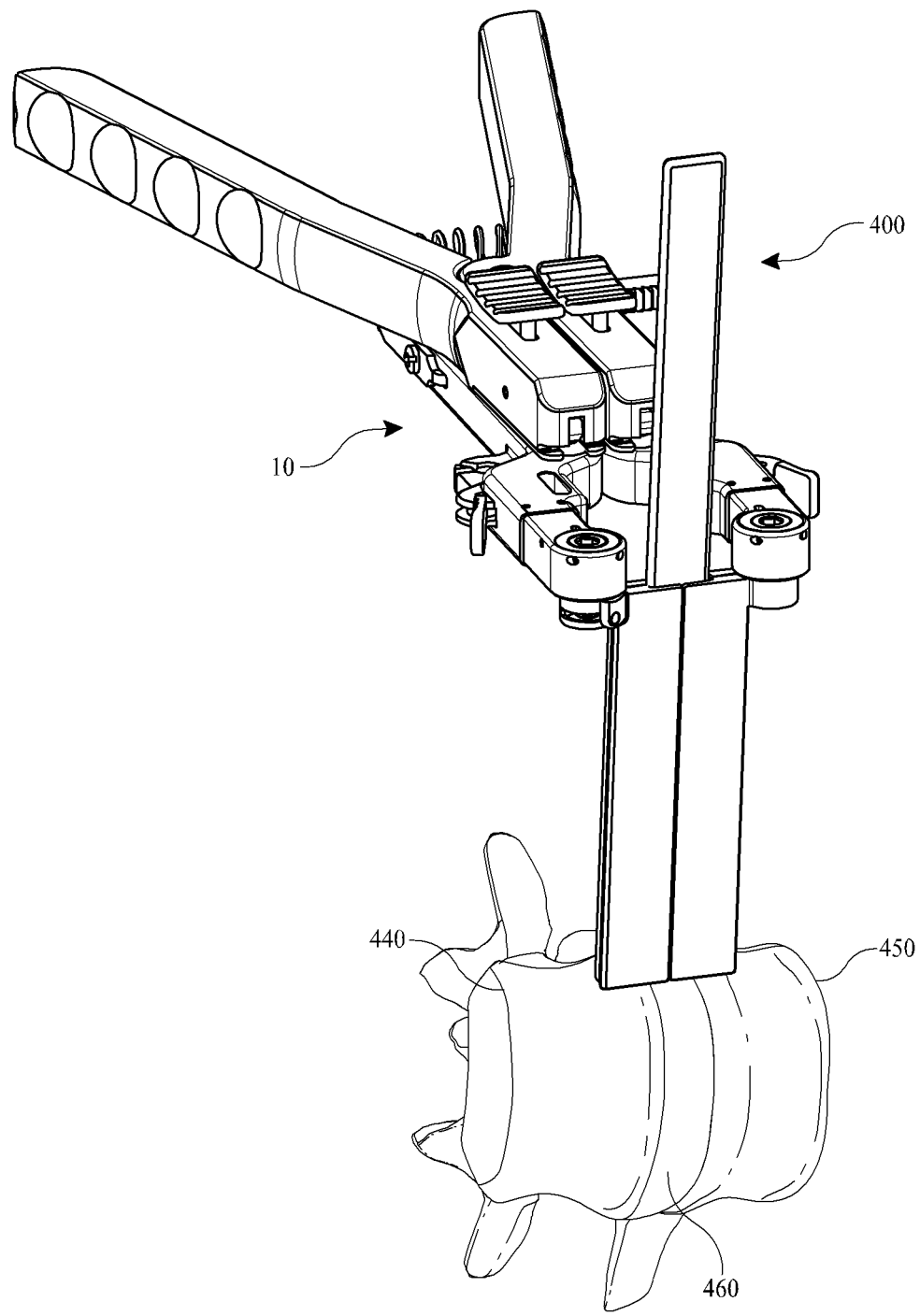
Figure 36E:
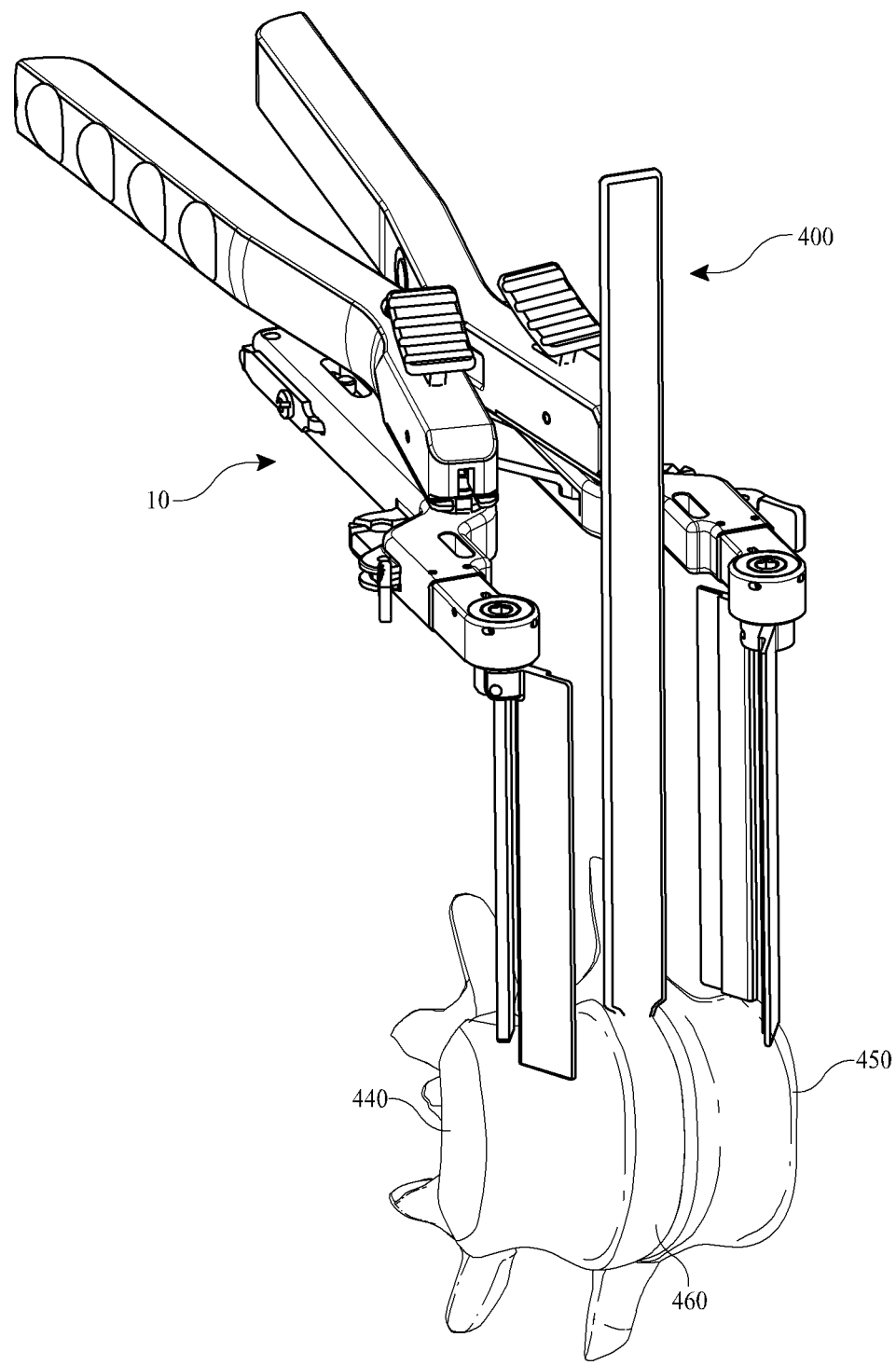

FIG. 36D illustrates the retractor 10 and placed probe 400 of FIG. 36C where the blades of the retractor 10 in their closed conformation have been placed around the probe 400 and slipped down around the probe 400 into the channel already formed by the probe 400 in the patient, to the spine. FIG. 36D shows the retractor 10 still in its closed conformation and the blades still in their closed conformation such that the blades substantially closely enclose the probe 400. FIG. 36E illustrates the same retractor 10 of FIG. 36D where the retractor 10 has been engaged and the blades have been deployed (both as have been disclosed fully above) to pull open the incision formed by the insertion of the probe 400.

Figure 36F:
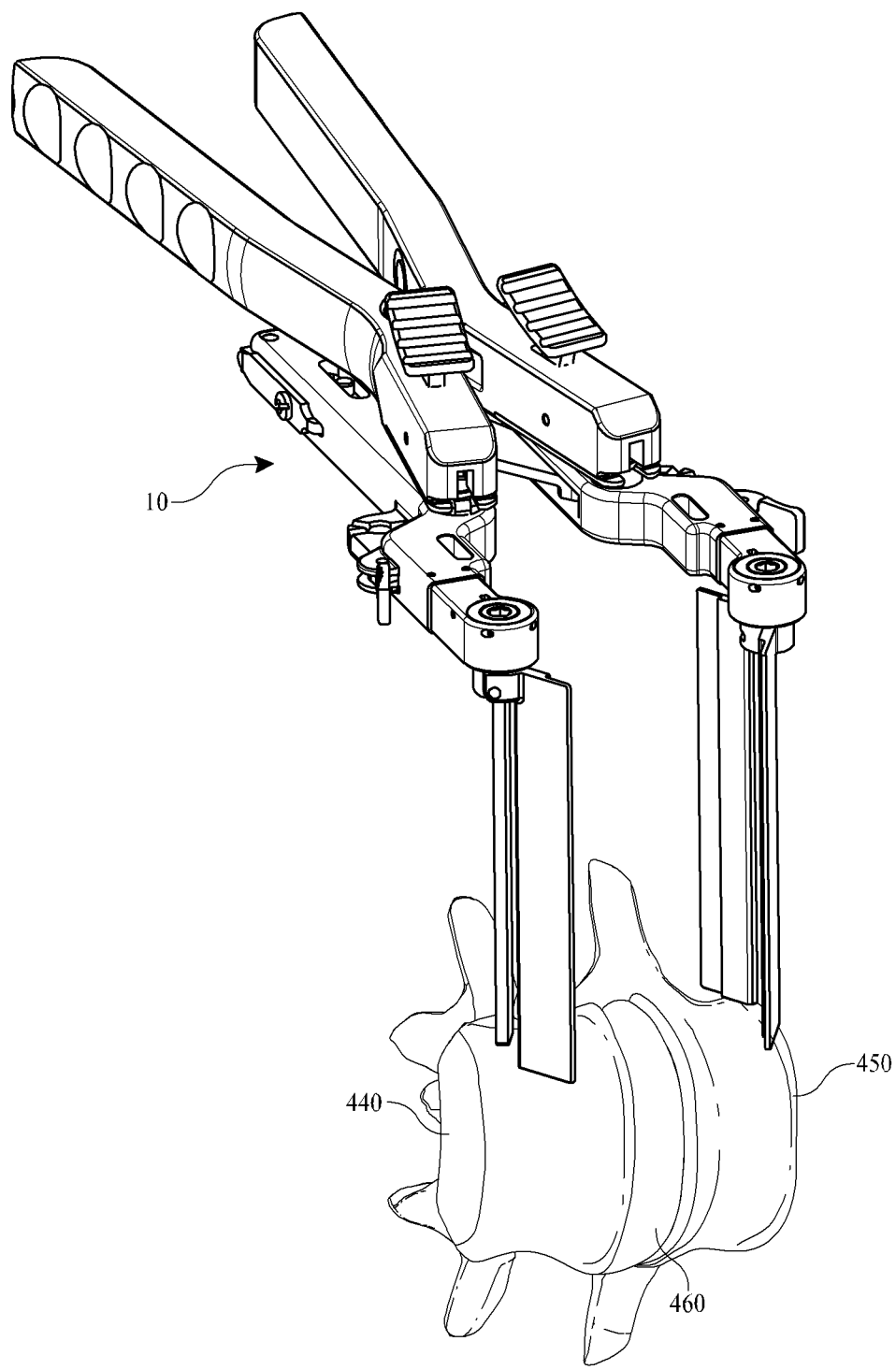

FIG. 36F illustrates the retractor 10 and blades in place prepared for physician access to the desired spinal location wherein the probe 400 has been removed for physician access. The probe 400 can allow a surgeon to easily and quickly insert a retractor 10 without cutting an incision all the way to the surgery site prior to inserting the retractor 10 into the desired location to access the surgery site. Rather, the surgeon can quickly and easily insert the probe 400 into the desired location, anchor the probe 400 using the anchor tip 430 in the desired location, slip the blades of the retractor 10 around the probe 400, and then simply slip the retractor 10 into place at which point in time the retractor and blades can be engaged to open up the surgical site and the probe 400 may be removed.

Figure 37C:
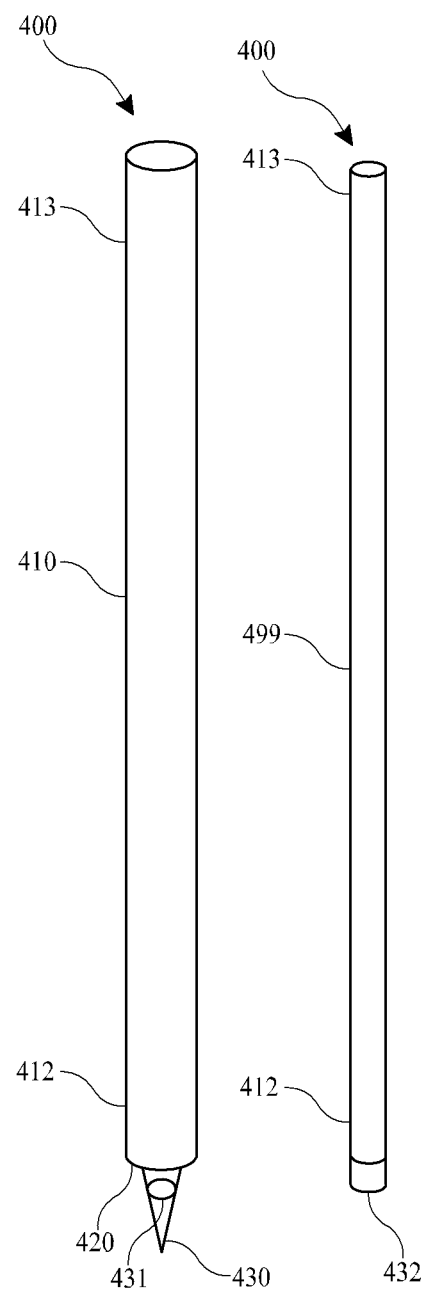
Figure 37D:
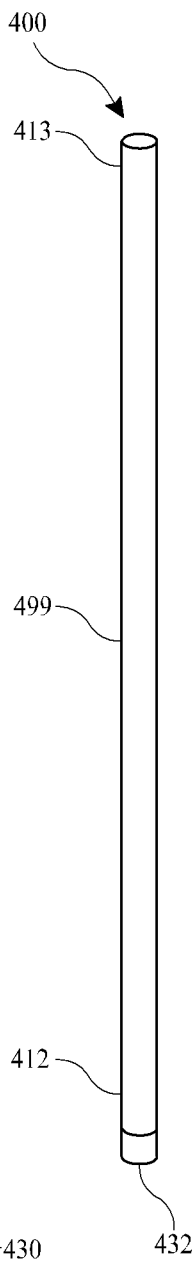
Figure 38A:
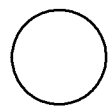
FIGS. 38A-38I show various cross sections of a probe system.
Figure 38F:
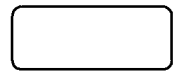
Figure 38B:
Figure 38G:
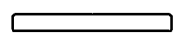
Figure 38C:
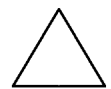
Figure 38H:
Figure 38D:
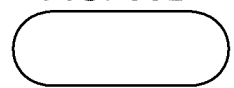
Figure 38I:
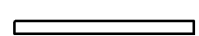
Figure 38E:

In one embodiment, the probe 400 comprises at least one electrode, wherein the at least one electrode is capable of stimulating a nerve to provoke an electromyographic response in the nerve. FIG. 37C illustrates a probe 400 with an electrode 431 disposed at the distal end 412 of the probe 400 on the anchor tip 430. In some embodiments, only one electrode is used. In other embodiments, a plurality of electrodes can be used, including about 1-10 electrodes, about 2-8 electrodes, about 3-6 electrodes and about 4-5 electrodes. In some embodiments, at least one electrode can be disposed on the anchor tip 430. In some embodiments, at least one electrode can be disposed on the probe body 410. The electrod 431 can be allowed to any of the embodiments described hering In some embodiments, the probe 400 comprises an endoscope 499, wherein the endoscope 499 can comprise an imaging element 432 at the distal end 412 of the endoscope 499. In some of these embodiments, the endoscope 499 can be configured to both allow a surgeon to visualize the placement of the probe 400 as well as allow a surgeon to slide a retractor 10 down over the probe 400 and into place as described herein to create an operative channel. In some embodiments, the endoscope 499 can include an anchor tip 430. Such an endoscope can be applied to any of the embodiments described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A retractor comprising:
   a first blade;
   a first rotation mechanism configured to rotate the first blade clockwise and counterclockwise about a first axis;
   a second blade;
   a second rotation mechanism configured to rotate the second blade clockwise and counterclockwise about a second axis;
   wherein the first blade and the second blade are parallel in a closed blade assembly to slide relative to a probe toward a patient, wherein the first blade and the second blade are configured to rotate after sliding relative to the probe.

2. The retractor of claim 1, further comprising a third blade.

3. The retractor of claim 1, wherein the first axis and the second axis are parallel.

4. The retractor of claim 1, wherein separation of the first blade and the second blade is independent of rotation of the first blade and rotation of the second blade.

5. The retractor of claim 1, wherein the first blade and the second blade rotate in opposite directions to open.

6. The retractor of claim 1, wherein the first blade is configured to rotate clockwise and the second blade is configure to rotate counterclockwise.

7. The retractor of claim 1, wherein the first rotation mechanism comprises a threaded component.

8. The retractor of claim 1, wherein the first rotation mechanism comprises a pin and a groove.

9. The retractor of claim 1, wherein first rotation mechanism is a mirror image of the second rotation mechanism.

10. The retractor of claim 1, wherein rotation of the first blade is independent of rotation of the second blade.

11. The retractor of claim 1, wherein the first blade and the second blade are configured to separate after sliding relative to the probe.

12. The retractor of claim 1, further comprising the probe.

13. The retractor of claim 1, further comprising one or more additional blades.

14. The retractor of claim 1, further comprising an actuator configured to move both the first blade and second blade about a trajectory.

15. The retractor of claim 14, wherein the trajectory moves the first blade and the second blade away from a location of interest.

16. The retractor of claim 14, wherein the trajectory is transverse to the first axis.

17. The retractor of claim 1, further comprising an actuator configured to separate the first blade and the second blade.

* * * * *

UNITED STATES PATENT AND TRADEMARK OFFICE
CERTIFICATE OF CORRECTION

PATENT NO. : 11,801,042 B2
APPLICATION NO. : 17/126791
DATED : October 31, 2023
INVENTOR(S) : Jason Blain Page 1 of 1

It is certified that error appears in the above-identified patent and that said Letters Patent is hereby corrected as shown below:

In the Claims

Column 28, Line 18 (approx.), Claim 6, delete "configure" and insert -- configured --.

Signed and Sealed this
Twenty-first Day of January, 2025

Coke Morgan Stewart
*Acting Director of the United States Patent and Trademark Office*